United States Patent [19]
Pittet et al.

[11] Patent Number: 4,521,613
[45] Date of Patent: Jun. 4, 1985

[54] 4(HYDROCARBYLTHIO)ACETOACETIC ESTERS

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 589,575

[22] Filed: Mar. 14, 1984

[51] Int. Cl.³ .................... C07C 149/20; A23L 1/226
[52] U.S. Cl. ........................................ 560/152; 426/3; 426/535
[58] Field of Search ......................... 560/152

[56] References Cited

U.S. PATENT DOCUMENTS 2,828,321 3/1958 Bullock ........................... 560/152 X
3,061,619 10/1962 Braunwarth et al. ........... 560/152 X

FOREIGN PATENT DOCUMENTS 2554703 6/1977 Fed. Rep. of Germany .

OTHER PUBLICATIONS

Chemical Abstracts, vol. 72, 1970, abstract No. 90181y, Trofimov et al.
Chemical Abstracts, vol. 87, 1977, abstract No. 152195b, Moeller et al.

Primary Examiner—Natalie Trousof
Assistant Examiner—Patricia M. Scott
Attorney, Agent, or Firm—Arthur L. Liberman

[57] ABSTRACT

Described is the genus of 4(hydrocarbylthio)acetoacetic esters defined according to the structure:

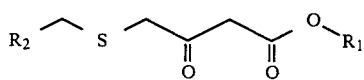

wherein $R_1$ represents $C_2$–$C_6$ aliphatic hydrocarbyl and $R_2$ represents hydrogen or $C_1$–$C_2$ aliphatic hydrocarbyl and the uses of such 4(hydrocarbylthio)acetoacetic esters for augmenting or enhancing the aroma or taste of foodstuffs and chewing gums.

6 Claims, 23 Drawing Figures

FIG.1
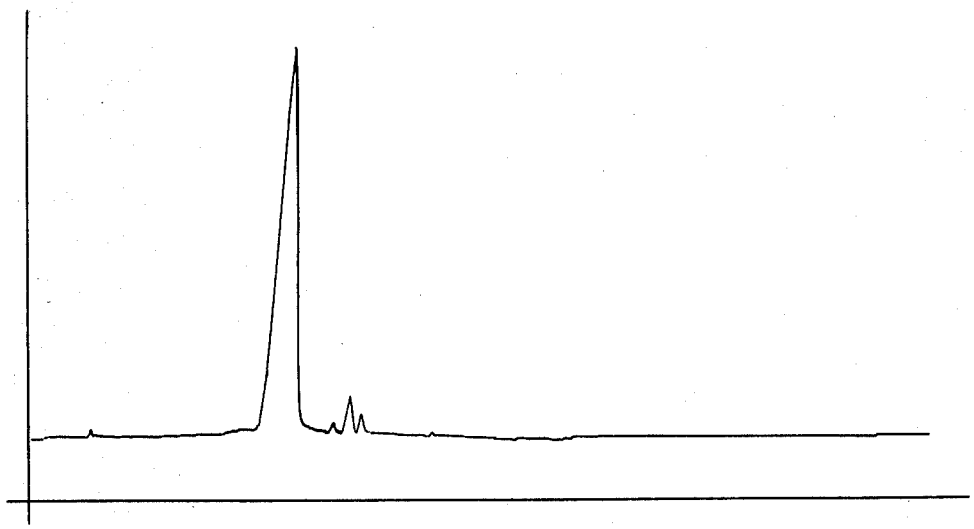
GLC PROFILE FOR FRACTION 6 OF EXAMPLE I.
GLC PROFILE FOR FRACTION 5 OF EXAMPLE II.
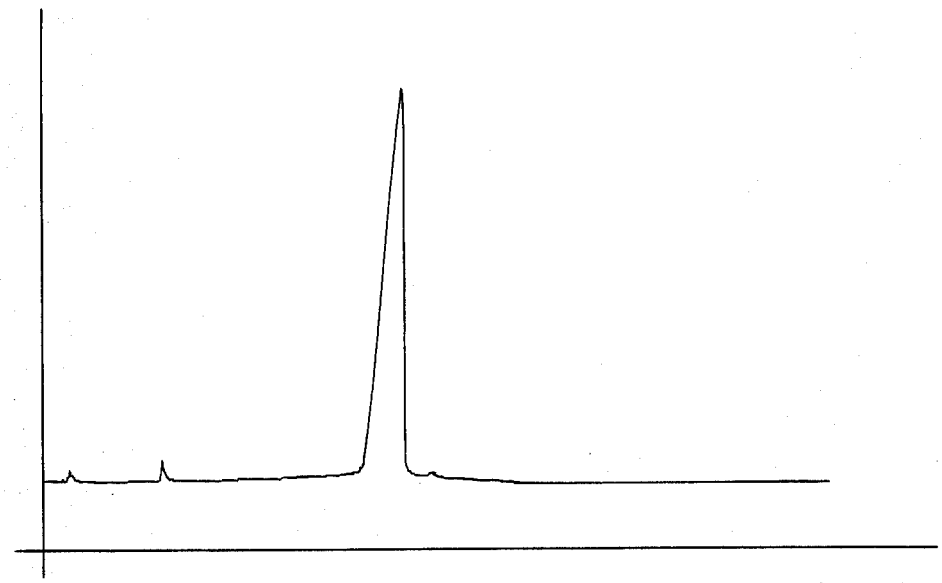
FIG.3

NMR SPECTRUM FOR EXAMPLE I.

FIG. 5
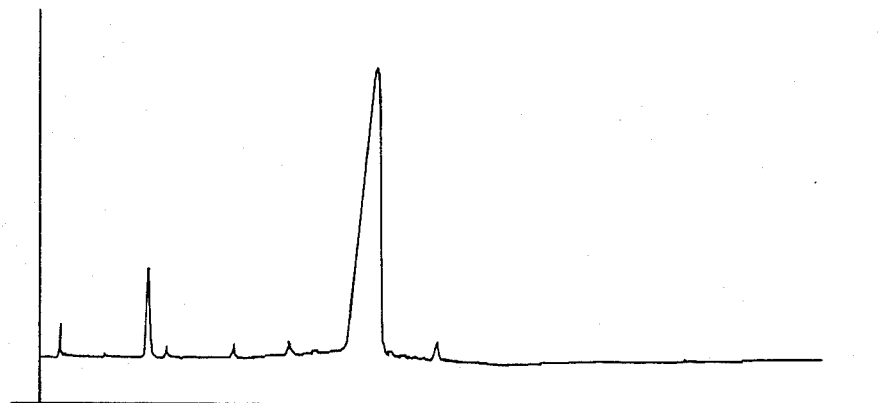
GLC PROFILE FOR FRACTION 3 OF EXAMPLE III.
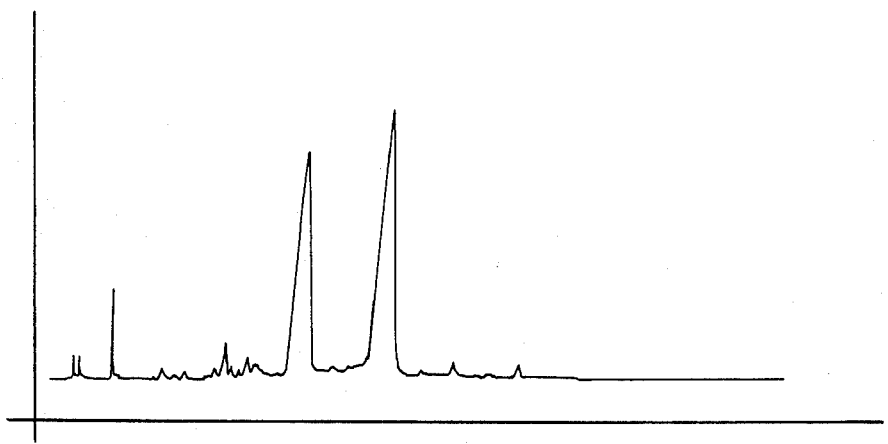
GLC PROFILE FOR FRACTION 2 OF EXAMPLE IV.
FIG. 7

FIG.8
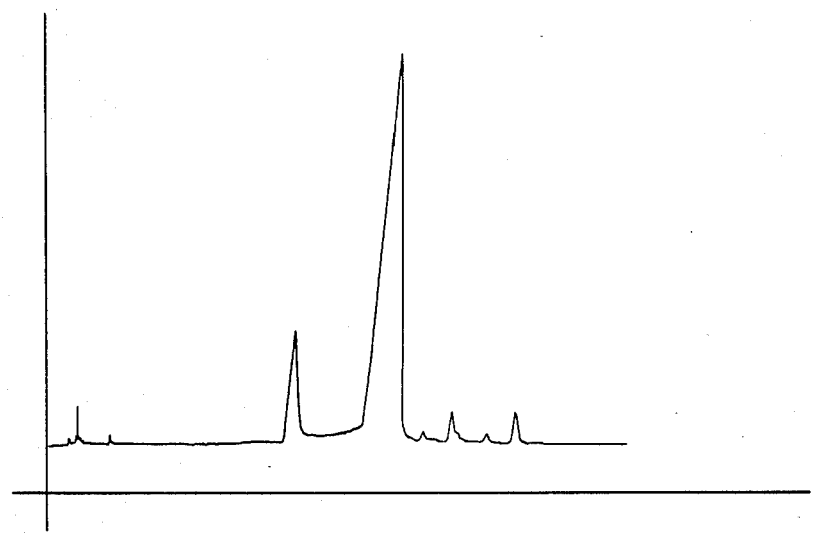
GLC PROFILE FOR FRACTION 3 OF EXAMPLE IV.
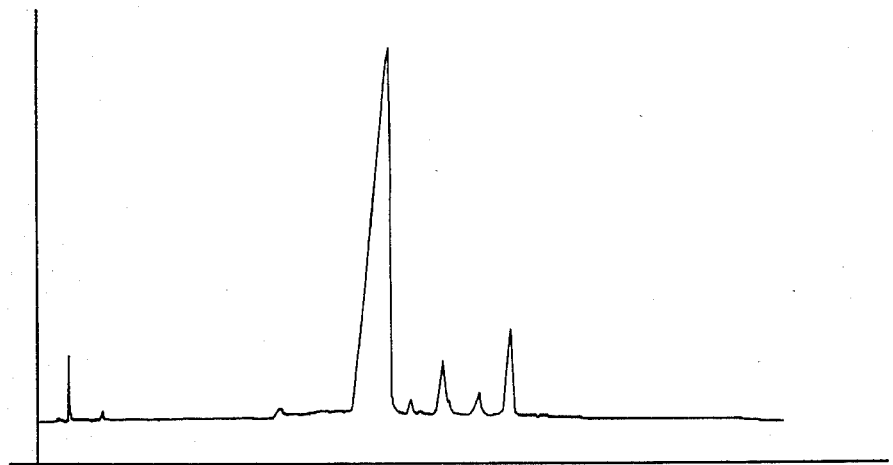
GLC PROFILE FOR FRACTION 4 OF EXAMPLE IV.
FIG.9

FIG.10 NMR SPECTRUM FOR FRACTION 4 OF EXAMPLE IV.

FIG.11
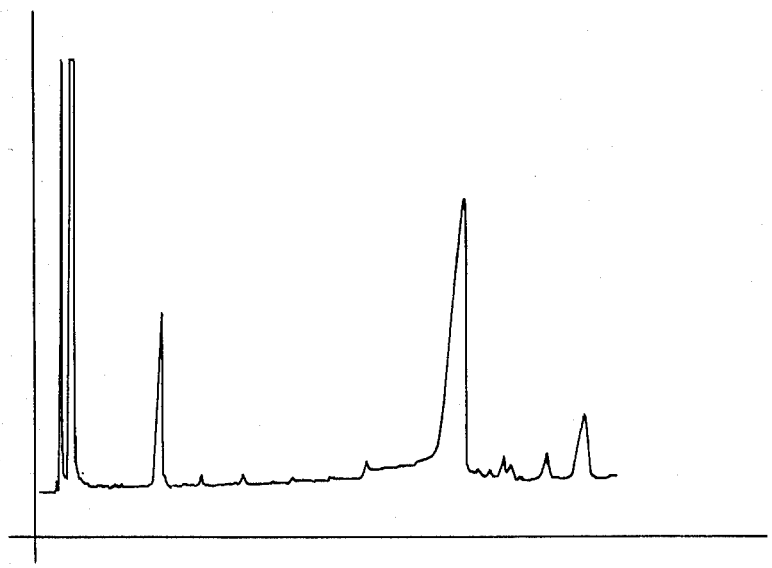
GLC PROFILE FOR EXAMPLE V.
CRUDE
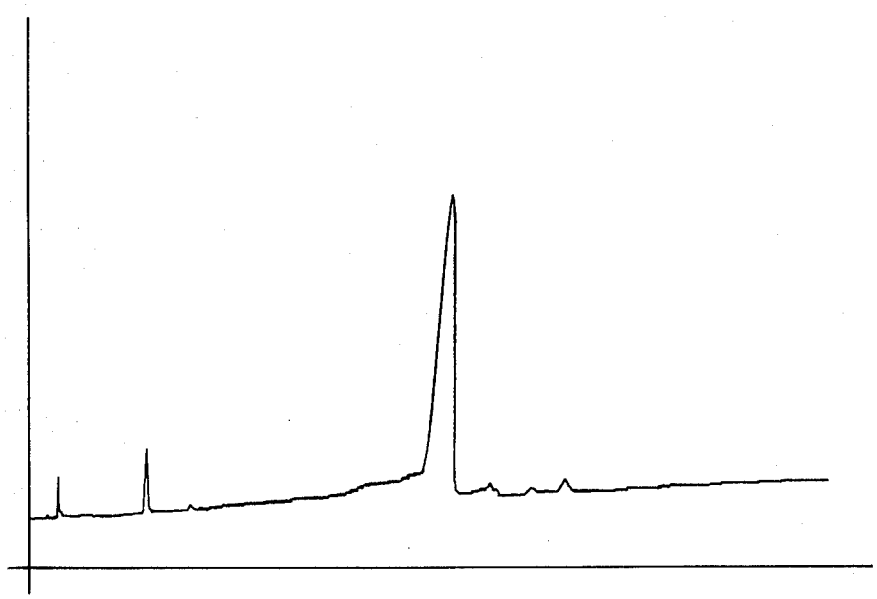
GLC PROFILE FOR FRACTION 2 OF
EXAMPLE V.
FIG.12

FIG. 13 NMR SPECTRUM FOR FRACTION 2 OF EXAMPLE V.

FIG. 14
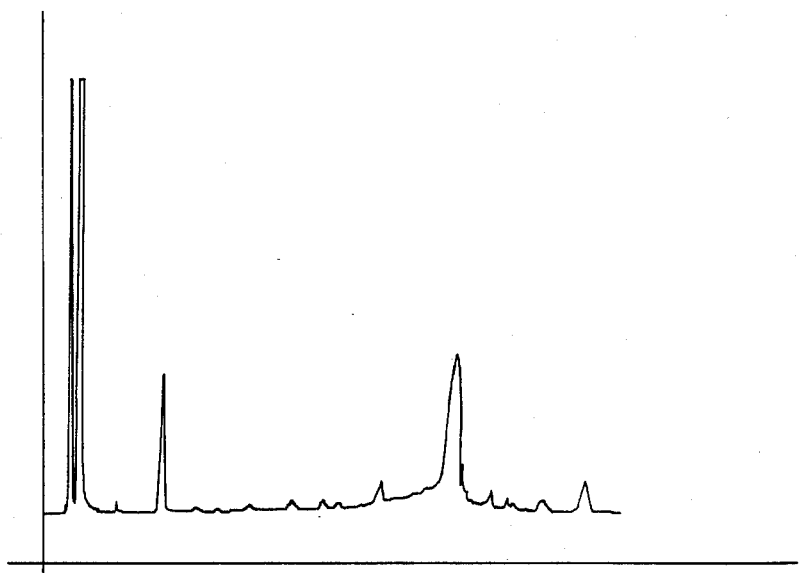
GLC PROFILE FOR EXAMPLE VI.
CRUDE
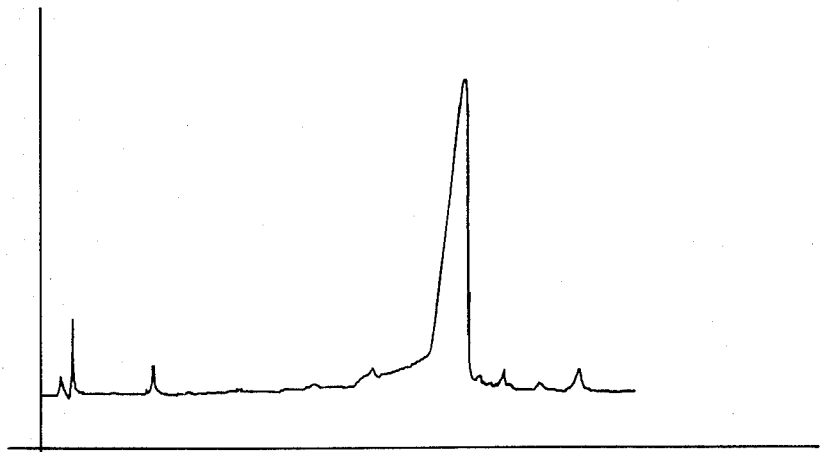
GLC PROFILE FOR FRACTION 4 OF
EXAMPLE VI.
FIG. 15

FIG.17
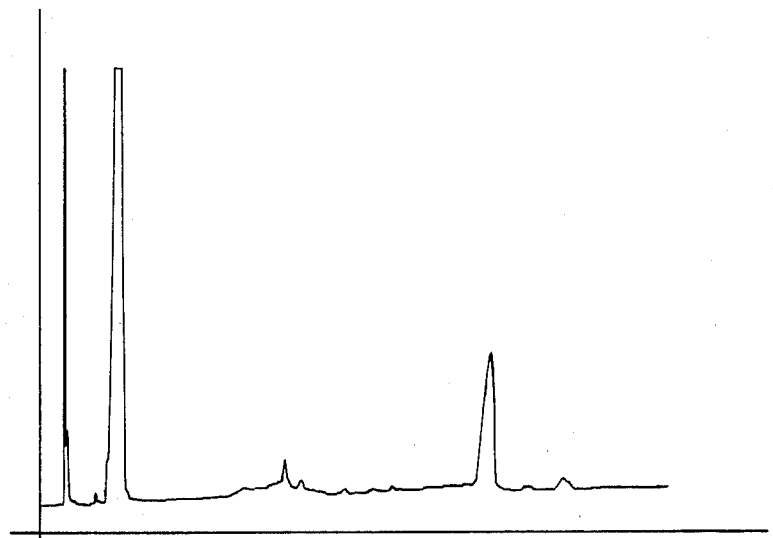
GLC PROFILE FOR EXAMPLE VII.
CRUDE
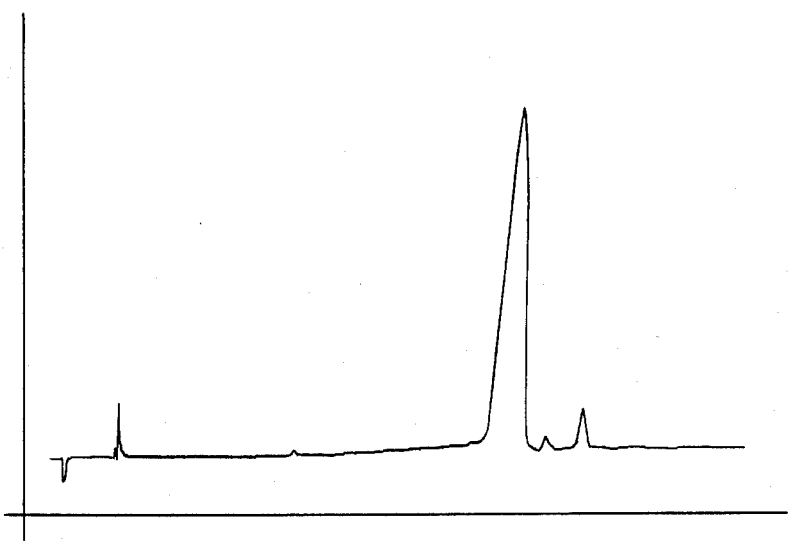
GLC PROFILE FOR FRACTION 5 OF
EXAMPLE VII.
FIG.18

FIG. 20
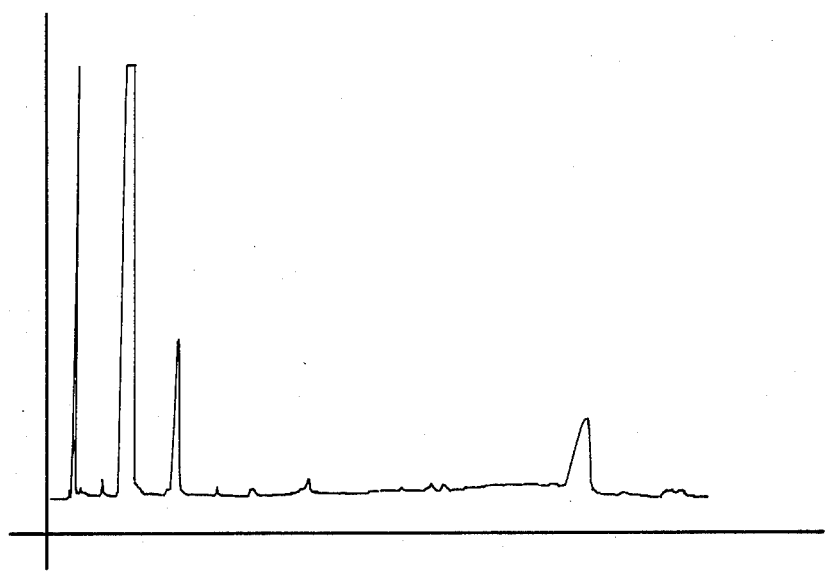
GLC PROFILE FOR EXAMPLE VIII.
CRUDE
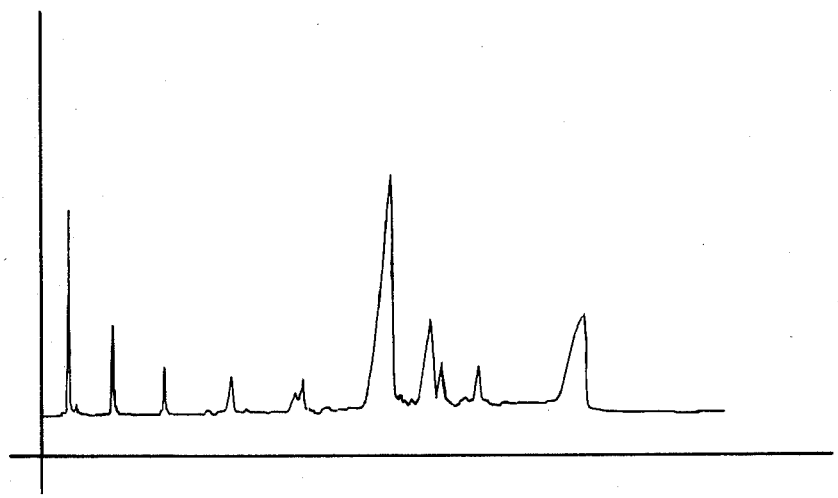
GLC PROFILE FOR FRACTION 3 OF
EXAMPLE VIII.
FIG. 21

GLC PROFILE FOR FRACTION 4 OF EXAMPLE VIII.

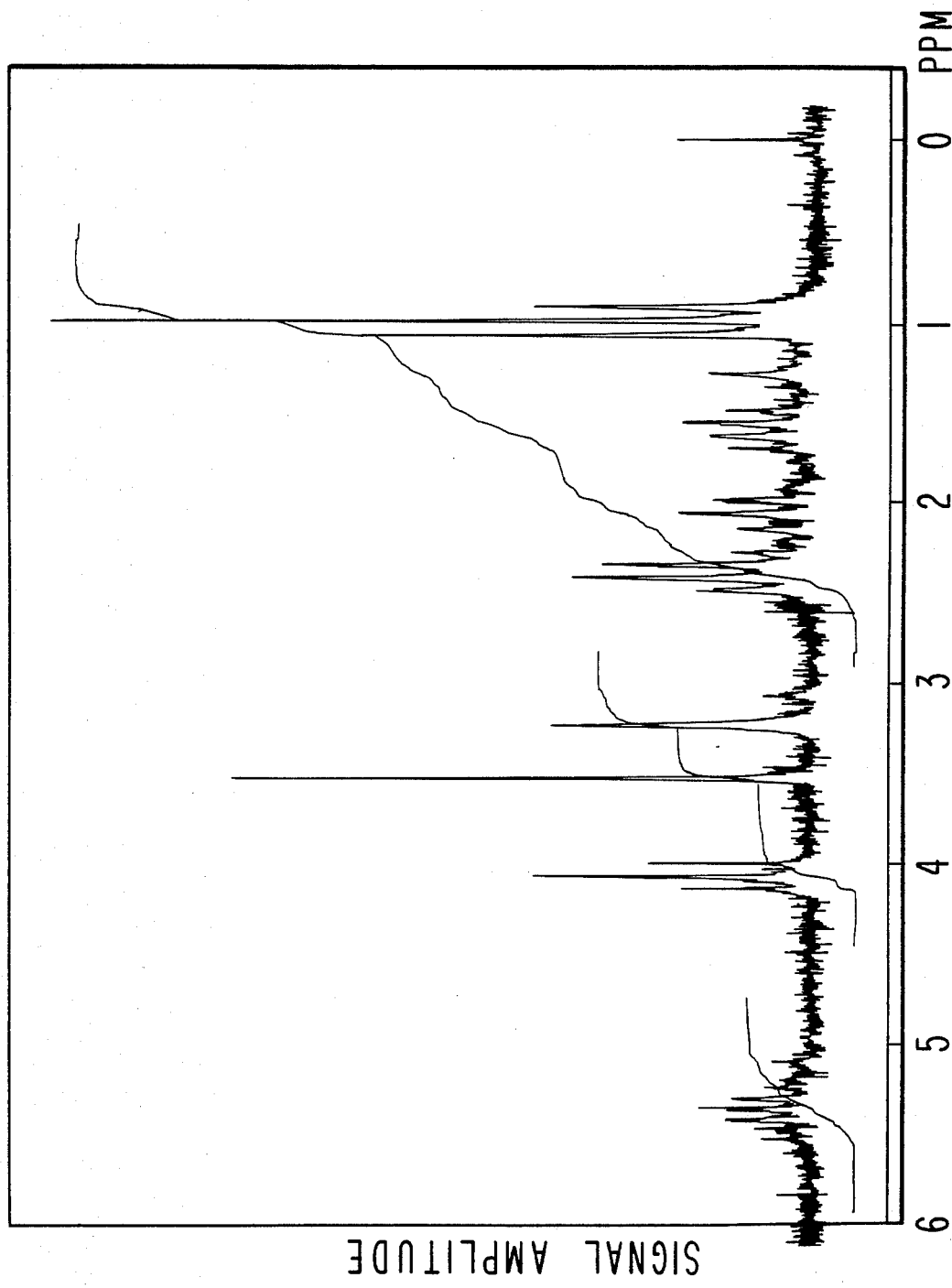
FIG. 23 NMR SPECTRUM FOR FRACTION 4 OF EXAMPLE VIII.

4(HYDROCARBYLTHIO)ACETOACETIC ESTERS

BACKGROUND OF THE INVENTION

The instant invention relates to 4(hydrocarbylthio)acetoacetic esters defined according to the genus:

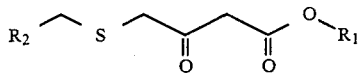

wherein $R_1$ represents $C_2$-$C_6$ aliphatic hydrocarbyl and $R_2$ represents hydrogen or $C_1$-$C_2$ aliphatic hydrocarbyl and uses thereof in augmenting or enhancing the aroma or taste of foodstuffs and chewing gums.

There is a continuous search for food flavor compositions which can vary, fortify, modify, enhance, augment or otherwise improve the flavor and/or aroma of foodstuffs and chewing gums. To be satisfactory, such compositions should be stable, non-toxic and blendable with other ingredients to provide their own unique flavor and aroma nuances without detracting from the co-ingredients of the formulations in which they are used. Preferably, such compositions should be naturally occurring or present in natural foodstuffs so that their ingestible safety can be readily recognized. These materials should be capable of being synthesized in a simple and economical manner. Thus, the need for safe flavors in the mushroom, gooseberry, broccoli, pineapple, onion, cashew juice, tropical fruit, apricot, kiwi, sour cream, dairy, salt substitute, strawberry, plum, tomato, green pepper, garlic and potato flavor area is well known, particularly in the ice cream, yogurt flavor and flavored gelatin dessert areas. More specifically, there is a need for the development of non-toxic materials, which can be used to replace natural materials not readily available having gooseberry, mushroom, broccoli, pineapple, fresh oniony, cashew juice-like, fruity, green, apple, kiwi-like, earthy, radish, fresh green, juicy, ripe tomato-like, potato skin-like, green pepper, garlic and ripe plum-like aroma and taste nuances.

Hydrocarbyl substituted thioesters are known in the field of augmenting or enhancing the aroma and/or taste of foodstuffs and chewing gums. Thus, U.S. Pat. No. 3,904,556 issued on Sept. 9, 1975 (Class 252, subclass 522), a division of Ser. No. 301,524 (U.S. Pat. No. 3,870,800) discloses methylthio butanoic acid esters useful in augmenting or enhancing sweet, roasted, nut-like, dairy, vegetable, fruity, cheesey, and onion-like aromas and tastes. Reissue U.S. Pat. No. Re. 30,370 discloses thioesters such as methyl-3(ethylthio)thiopropionate, ethyl-3-(methylthio)thiopropionate, methyl-3-(methylthio)thiopropionate and ethyl 3(ethylthio)ethylthiopropionate in augmenting or enhancing various aroma and taste profiles, e.g., cabbage and cauliflower-like aroma and taste profiles. Reissue U.S. Pat. No. Re. 30,370 is a reissue of U.S. Pat. No. 3,879,562 (Class 426, subclass 535).

Furthermore, furfuryl thioesters have been suggested in U.K. Pat. No. 1,156,480 for possible use in coffee flavors. Ethyl-α-methyldithiopropionate and ethyl-α-methyldithiosobutyrate have been said to possess green or onion-like fragrance notes and methanethiol benzoate, methanethiol isovalerate, methanethiol anteisovalerate, methanethiol butyrate, and methanethiol valerate have been said to have milky, rotten egg, cheese or gaseous, cabbage odor-flavor contributions in Netherlands Patent Application No. 68/12,899.

McFadden, et al., Analytical Chemistry 37,560, have suggested the presence of methyl thiohexanoate and thioheptanoate in oil derived from hops, and Buttery, et al., have reported similar work in J. Chromatography 18,399. Shultz, Day and Libbey, "The Chemistry and Physiology of Flavors", Westport, Conn.; Avi. Publishing Co., 1967, especially at page 452, disclose the presence in pineapple flavor of methyl-β-methylthiopropionate and ethyl-β-methylthiopropionate.

Nothing, however, in the prior art, discloses the 4(hydrocarbylthio)acetoacetic esters of our invention having the unexpected, unobvious and advantageous properties for use in augmenting or enhancing the organoleptic properties of foodstuffs and chewing gums.

BRIEF DESCRIPTION OF THE DRAWINGS

FIG. 1 is the GLC profile for fraction 6 of the distillation product of the reaction product of Example I containing the compound having the structure:

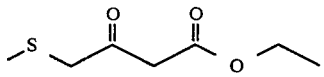

(Conditions: 10'×0.125" SE-30 column programmed at 120°-220° C. at 8° C. per minute).

Figure 2:
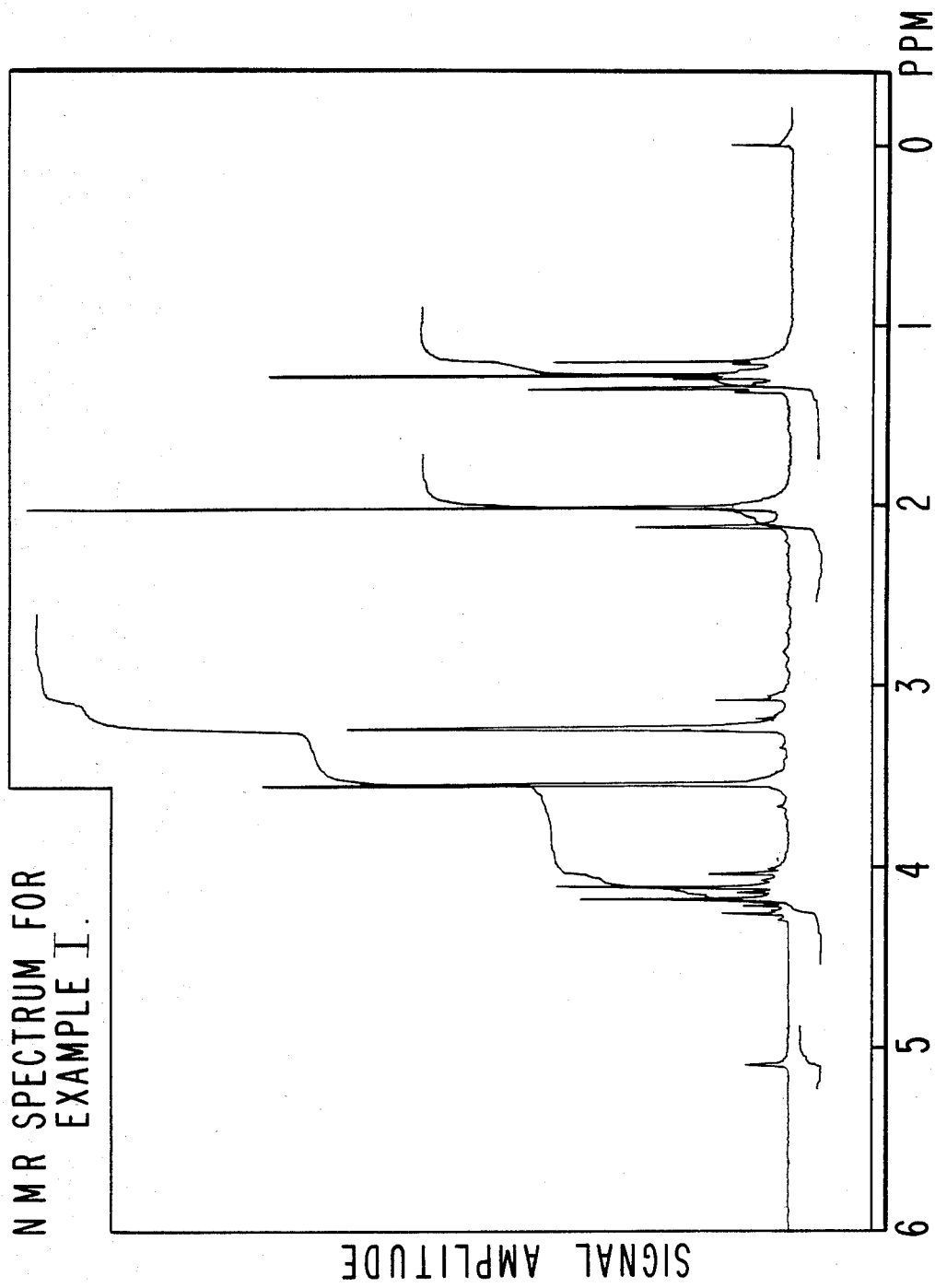

FIG. 2 is the NMR spectrum for the compound having the structure:

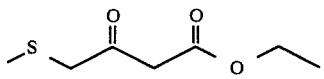

prepared according Example I (Conditions: Field strength: 100 MHz; solvent: CFCl₃).

FIG. 3 is the GLC profile for fraction 5 of the distillation product of the reaction product for Example II containing the compound having the structure:

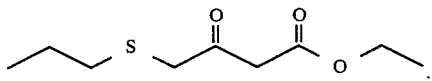

Figure 4:
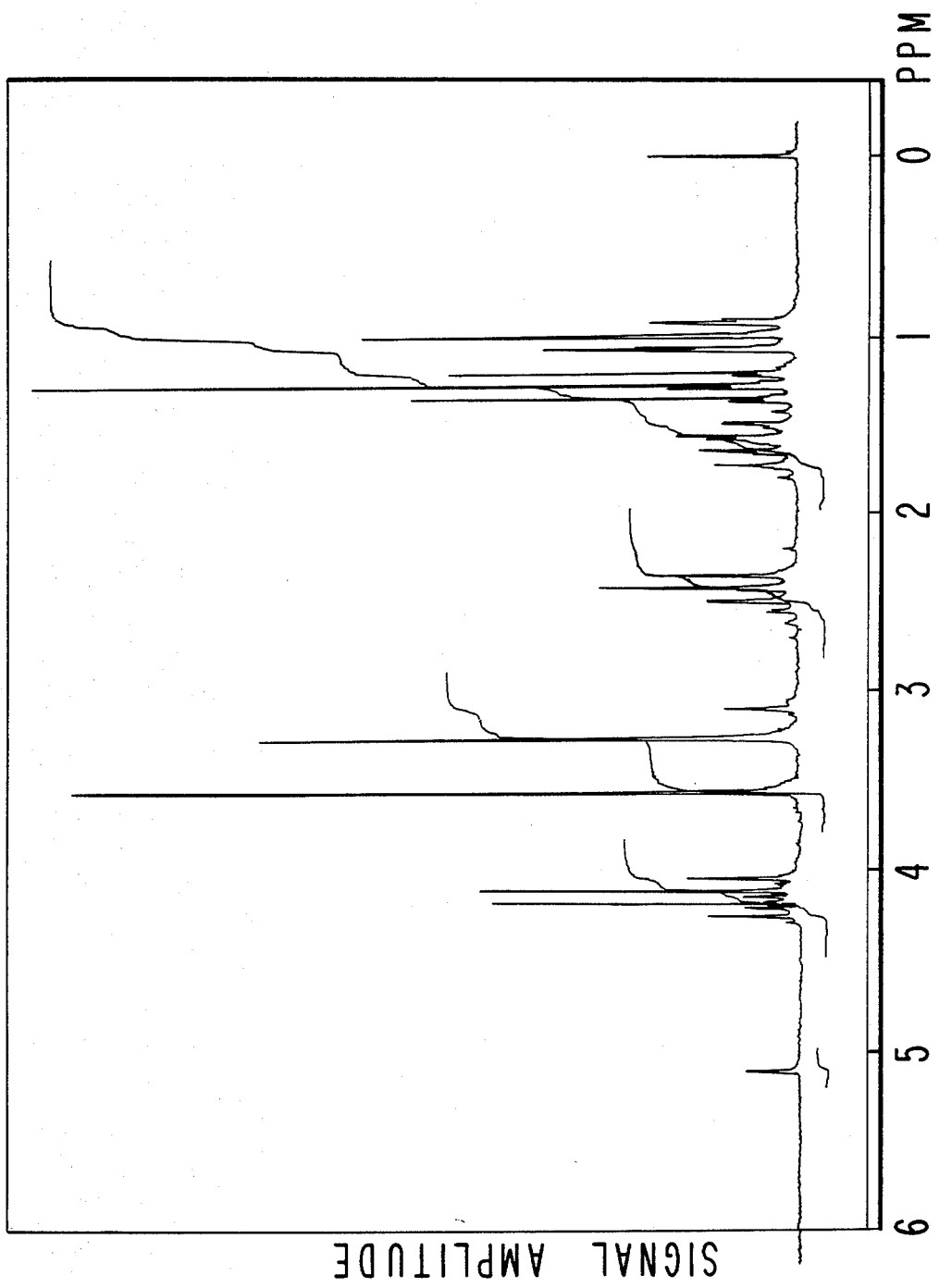

FIG. 4 is the NMR spectrum for fraction 5 of the distillation product of the reaction product of Example II containing the compound having the structure:

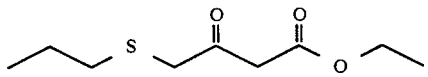

(Conditions: Field strength: 100 MHz; solvent: CFCl₃).

FIG. 5 is the GLC profile for fraction 3 of the distillation product of the reaction of Example III containing the compound having the structure:

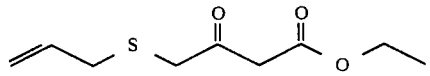

(Conditions: 10'×0.125" SE-30 column programmed at 100°-220° C. at 8° C. per minute).

Figure 6:
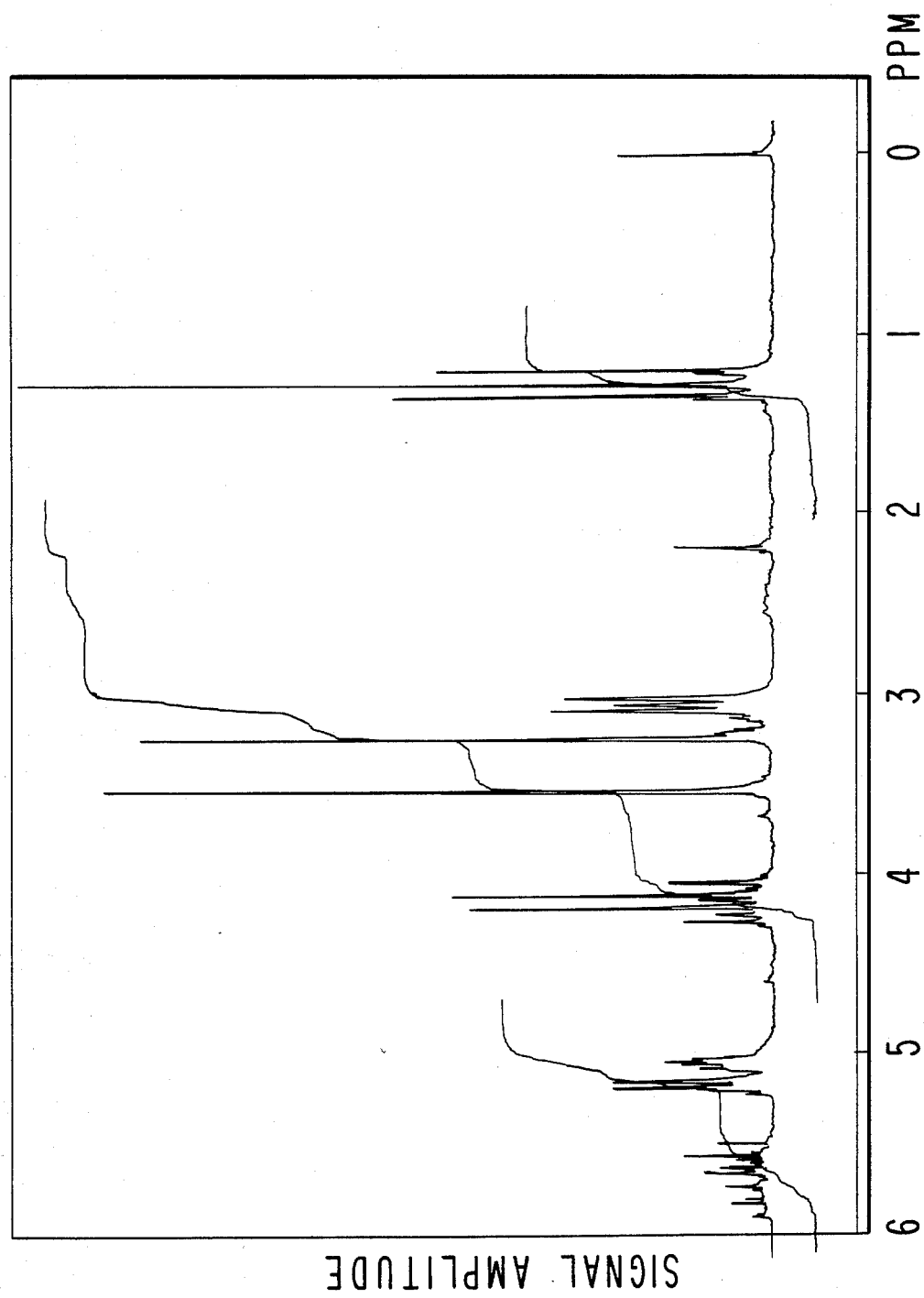

FIG. 6 is the NMR spectrum for fraction 3 of the distillation product of the reaction product of Example III containing the compound having the structure:

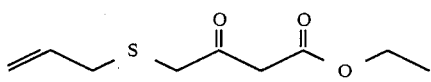

(Conditions: Field strength: 100 MHz; solvent: CFCl₃).

FIG. 7 is the GLC profile for fraction 2 of the distillation product of the reaction product of Example IV containing the compound having the structure:

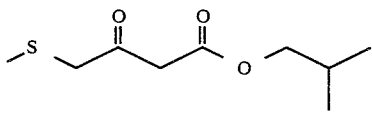

(Conditions: SE-30 10'×0.125" column programmed at 100°-220° C. at 8° C. per minute).

FIG. 8 is the GLC profile for fraction 3 of the distillation product of the reaction product of Example IV containing the compound having the structure:

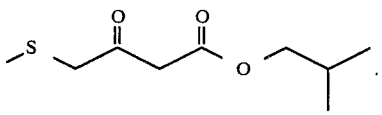

FIG. 9 is the GLC profile for fraction 4 of the distillation product of the reaction product of Example IV containing the compound having the structure:

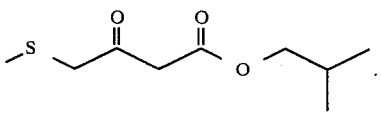

Figure 10:
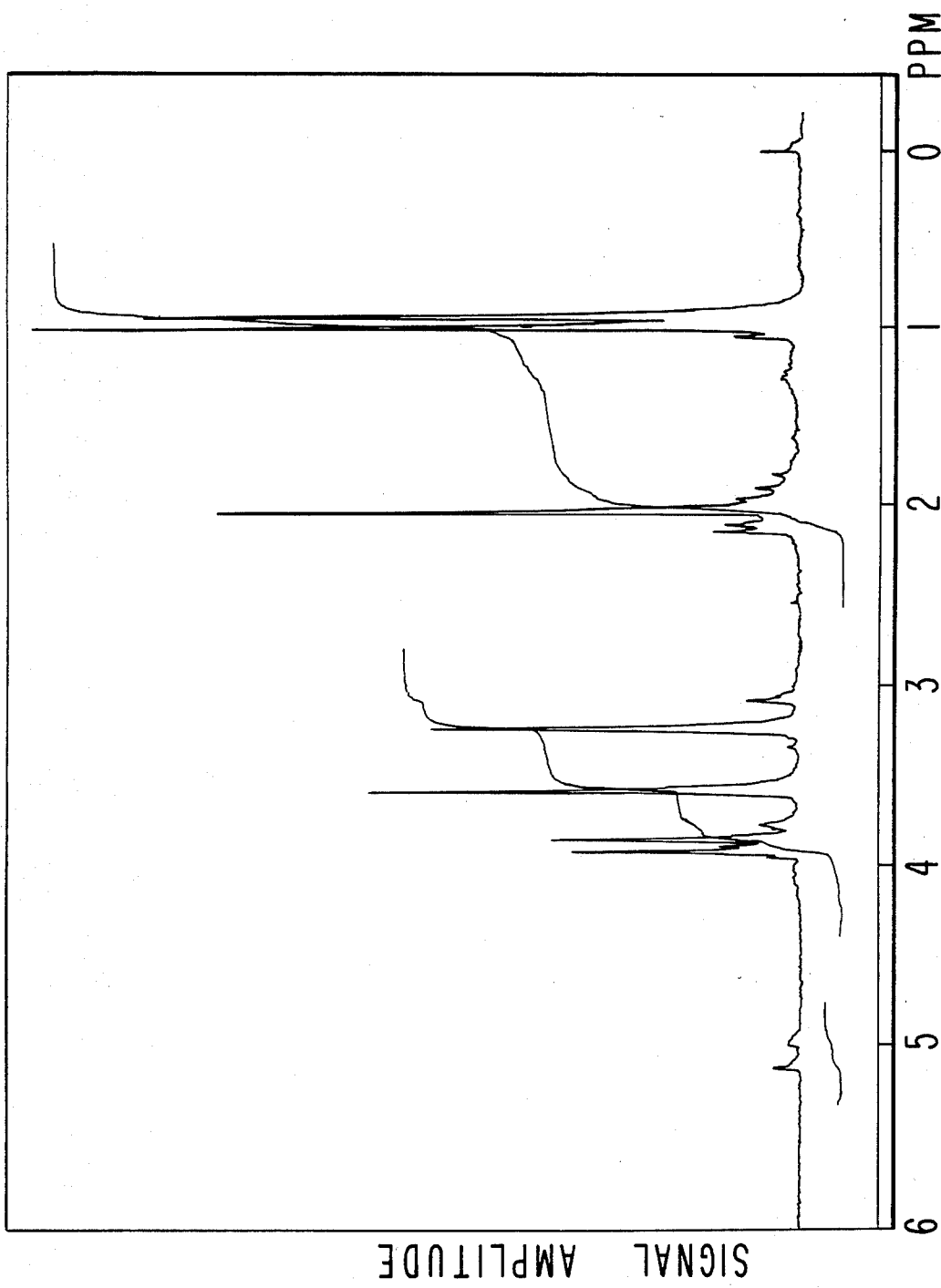

FIG. 10 is the NMR spectrum for fraction 4 of the distillation product of the reaction product of Example IV containing the compound having the structure:

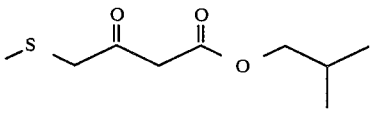

(Conditions: Field strength: 100 MHz; solvent: CFCl₃).

FIG. 11 is the GLC profile for the crude reaction product of Example V containing the product having the structure:

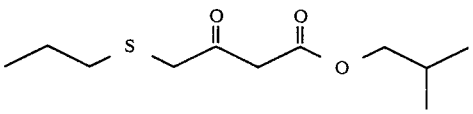

(Conditions: 10'×0.125" SE-30 column programmed at 100°-220° C. at 8° C. per minute).

FIG. 12 is the GLC profile for fraction 2 of the distillation product of the reaction product of Example V containing the compound having the structure:

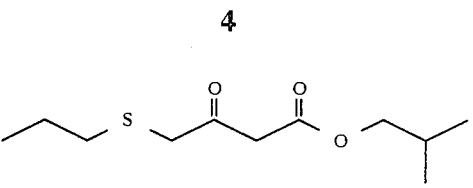

(Conditions: 10'×0.125" SE-30 column programmed at 100°-220° C. at 8° C. per minute).

Figure 13:
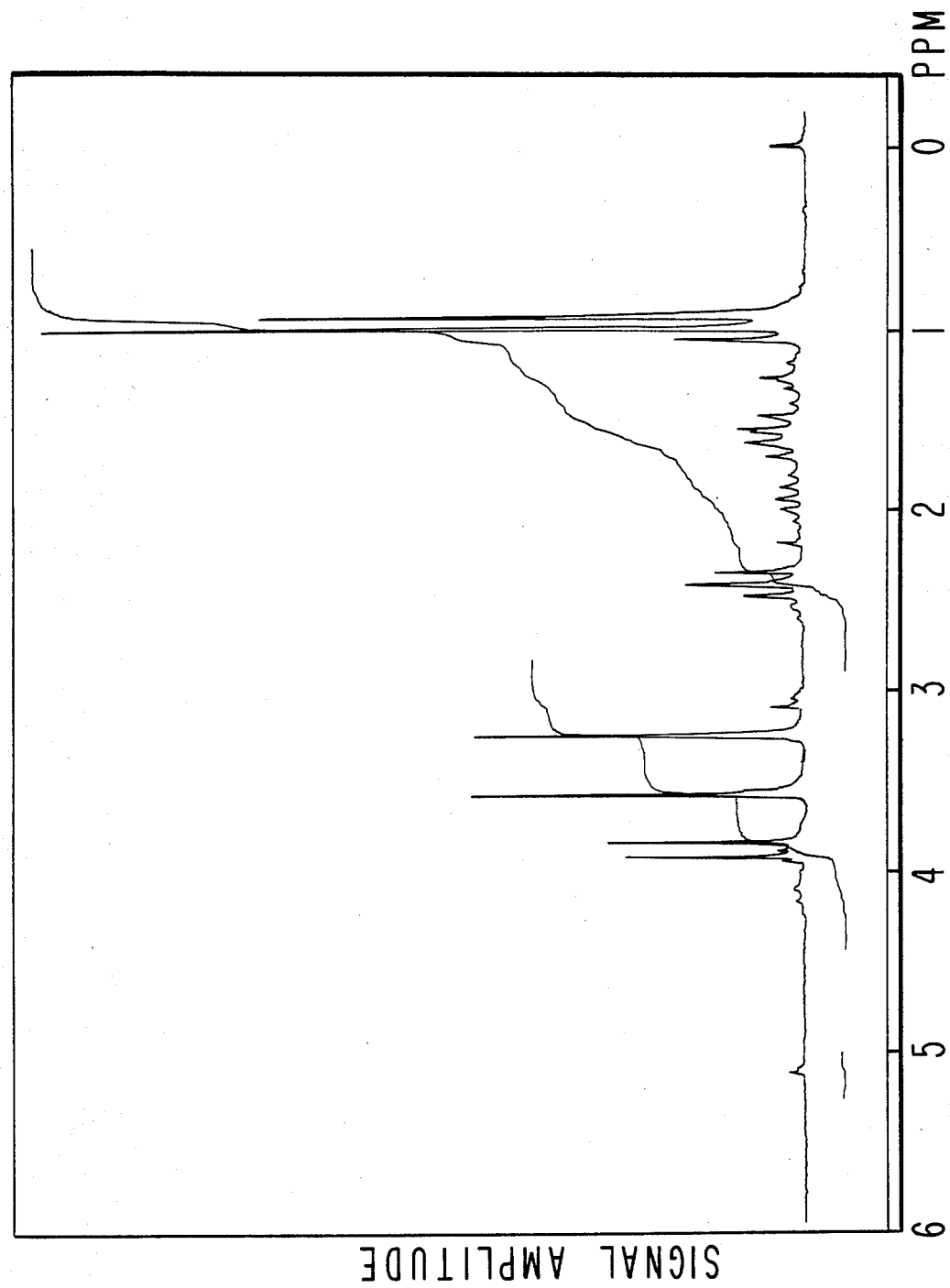

FIG. 13 is the NMR spectrum for fraction 2 of the distillation product of the reaction product of Example V containing the compound having the structure:

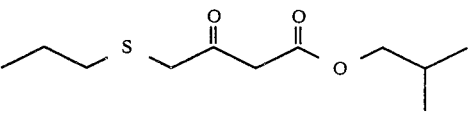

(Conditions: Field strength: 100 MHz; solvent: CFCl₃).

FIG. 14 is the GLC profile for the crude reaction product of Example VI containing the compound having the structure:

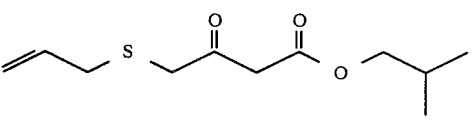

(Conditions: 10'×0.125" SE-30 column programmed at 100°-220° C. at 8° C. per minute).

FIG. 15 is the GLC profile for fraction 4 of the distillation product of the reaction product of Example VI containing the compound having the structure:

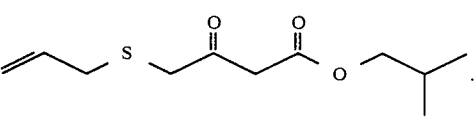

Figure 16:
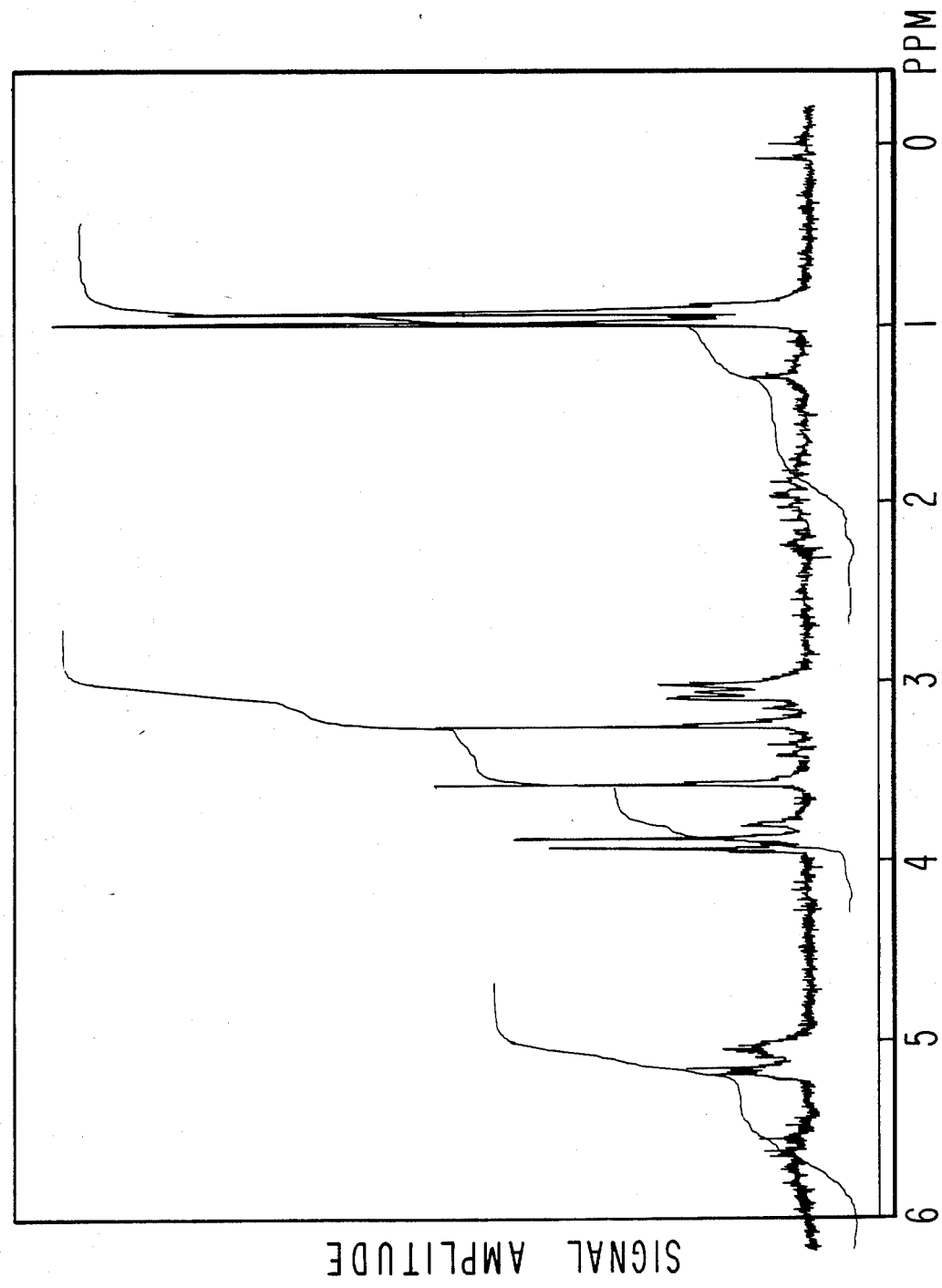

FIG. 16 is the NMR spectrum for fraction 4 of the distillation product of the reaction product of Example VI containing the compound having the structure:

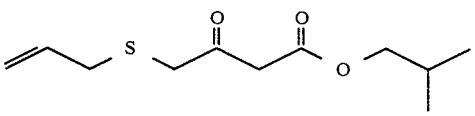

(Conditions: Field strength: 100 MHz; solvent: CFCl₃).

FIG. 17 is the GLC profile for the crude reaction product of Example VII containing the compound having the structure:

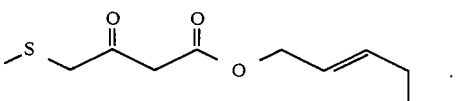

FIG. 18 is the GLC profile for fraction 5 of the distillation product of the reaction product of Example VII containing the compound having the structure:

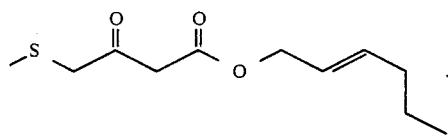

Figure 19:
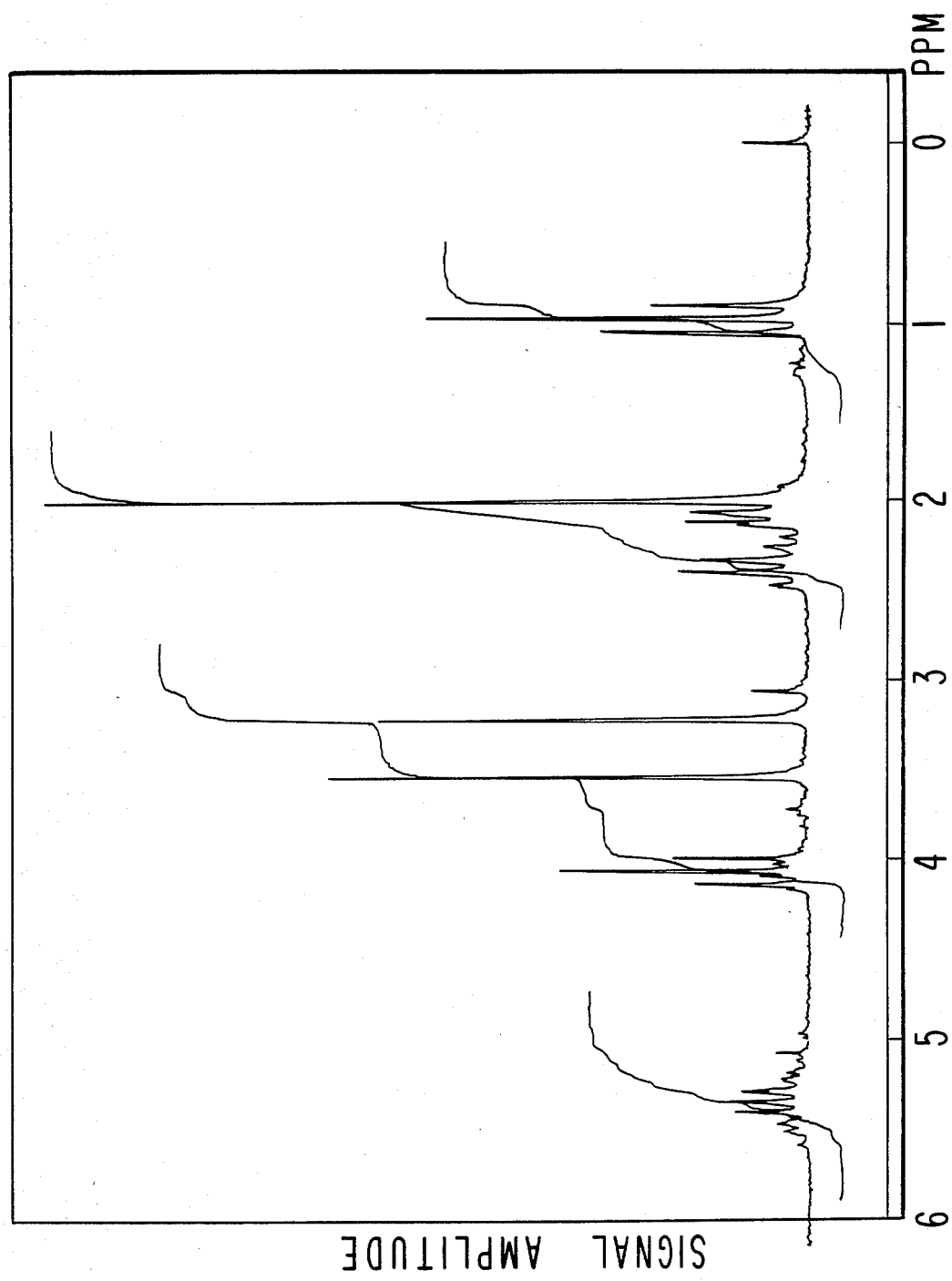

FIG. 19 is the NMR spectrum for fraction 5 of the distillation product of the reaction product of Example VII containing the compound having the structure:

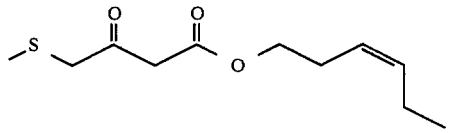

(Conditions: Field strength: 100 MHz; solvent: CFCl₃).

FIG. 20 is the GLC profile for the crude reaction product of Example VIII containing the compound having the structure:

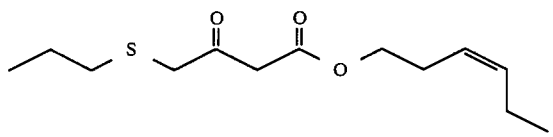

FIG. 21 is the GLC profile for fraction 3 of the distillation product of the reaction product of Example VIII containing the compound having the structure:

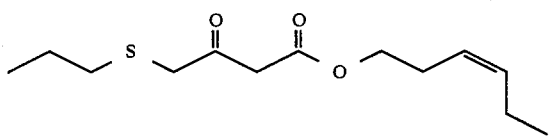

Figure 22:
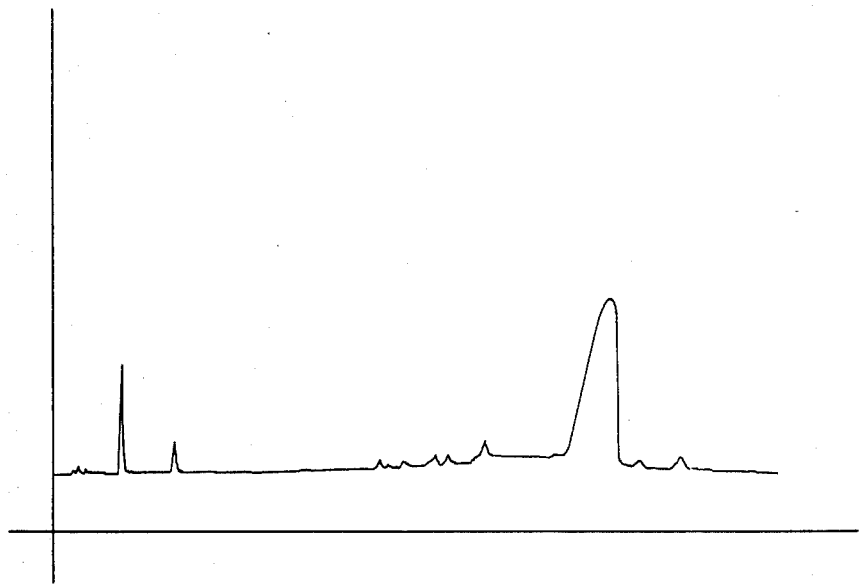

FIG. 22 is the GLC profile for fraction 4 of the distillation product of the reaction product of Example VIII containing the compound having the structure:

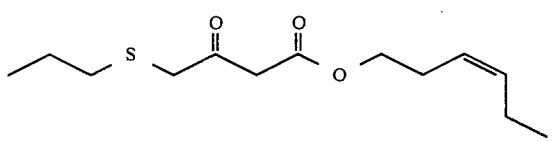

FIG. 23 is the NMR spectrum for fraction 4 of the distillation product of the reaction product of Example VIII containing the compound having the structure:

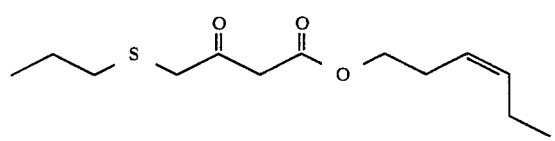

(Conditions: Field strength: 100 MHz; solvent: CFCl₃).

THE INVENTION

The present invention provides 4(hydrocarbylthio)acetoacetic esters defined according to the generic structure:

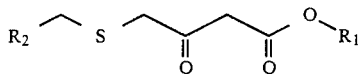

wherein $R_1$ is $C_2$–$C_6$ aliphatic hydrocarbyl and $R_2$ represents hydrogen or $C_1$–$C_2$ aliphatic hydrocarbyl.

The 4(hydrocarbylthio)acetoacetic esters of our invention produced according to the process of our invention are capable of augmenting or enhancing gooseberry, mushroom, broccoli, pineapple, fresh oniony, cashew juice, fruity, green, apple, kiwi, earthy, radish, salty, juicy, ripe tomato-like, potato skin-like, ripe plum-like, radish-like, green pepper and garlic aroma and taste characteristics in foodstuffs, foodstuff flavors, chewing gums and chewing gum flavors as well as toothpastes and toothpaste flavors.

Those compounds of our invention, which are defined according to the generic structure:

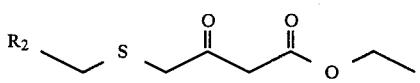

wherein $R_2$ represents hydrogen or $C_1$–$C_2$ aliphatic hydrocarbyl are synthesized by reacting the chloro derivatives of ethyl acetoacetate defined according to the structure:

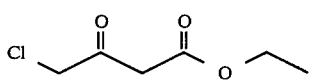

with a hydrocarbyl mercaptan defined according to the structure:

according to the reaction:

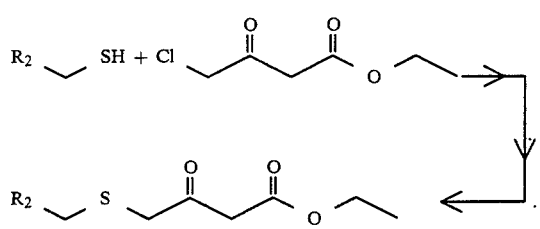

This reaction takes place in the presence of an alkali metal alkoxide, such as sodium methoxide, potassium methoxide or potassium t-butoxide. The reaction takes place at a temperature in the range of from about 20° C. up to about 50° C. The reaction may take place in the presence of an inert solvent or in the presence of excess mercaptan reactants defined according to the structure:

The mole ratio of the ethyl-4-chloroacetoacetate defined according to the structure:

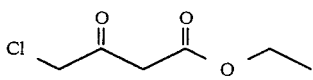

to hydrocarbyl mercaptan defined according to the structure:

may vary from about 1:1 up to about 1:5 with a preferred mole ratio of about 1:1:5. The mole ratio of ethyl-4-chloroacetoacetate:alkali metal alkoxide is preferably about 1:1. At the end of the reaction the reaction mass is extracted with an appropriate solvent, such as methylene dichloride and the methylene dichloride extract is then dried, filtered and evaporated. The resulting product is then distilled, preferably by means of fractional distillation to yield a flavor acceptable product.

The 4(hydrocarbylthio)acetoacetic esters of our invention defined according to the structure:

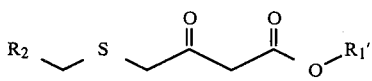

wherein $R_1'$ represents $C_3$–$C_6$ aliphatic hydrocarbyl and $R_2$ represents hydrogen or $C_1$ or $C_2$ aliphatic hydrocarbyl may be synthesized by reacting the compound defined according to the structure:

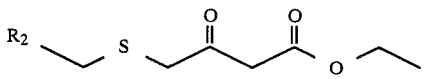

with an alcohol defined according to the structure:

according to the trans-esterification reaction, to wit:

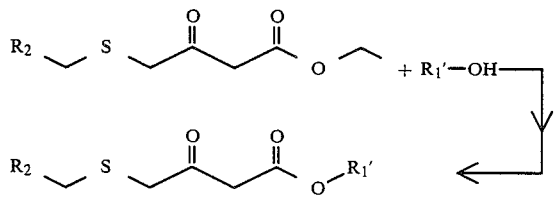

wherein $R_1'$ and $R_2$ are defined, supra. The trans-esterification reaction is carried out in the presence of a standard trans-esterification catalyst which is a protonic acid such as paratoluene, sulphonic acid or methane sulphonic acid. The mole ratio of the compound having the structure:

to thioester reactant defined according to the structure:

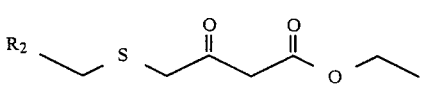

may vary from about 2:1 up to about 8:1 with a preferred mole ratio in the range of from about 4:1 up to about 6:1. The concentration of catalyst in the reaction mass may vary from about 0.2% up to about 1.0%. The trans-esterification reaction is preferably carried out at reflux conditions, e.g., from about 70° C. up to about 140° C. and from about atmospheric pressure up to about 5 atmospheres. The reflux conditions and consequently the reaction temperature, is a function of the reactants utilized. At the end of the trans-esterification reaction, the reaction mass is fractionally distilled and appropriate fractions are selected for use as flavor-acceptable fractions.

The following table sets forth specific 4(hydrocarbylthio)acetoacetic esters of our invention and their organoleptic properties.

TABLE I

| THE 4 (HYDROCARBYLTHIO) ACETOACETIC ESTERS OF OUR INVENTION | FLAVOR PROPERTIES |
|---|---|
| Compound having the structure: <br> prepared according to Example I | A gooseberry, mushroom-like broccoli-like and pineapple aroma and taste profile at 1 ppm causing it to be useful in gooseberry, mushroom broccoli and pineapple flavored foodstuffs. |
| Compound having the structure: <br> produced according to Example II | A fresh oniony aroma and taste profile at 1 ppm causing it to be useful in onion flavors. |
| Compound having the structure: <br> prepared according to Example III | A cashew juice aroma and taste profile at 0.001 ppm causing it to be useful in cashew juice, pineapple, tropical fruit, and apricot flavored foodstuffs. |
| Compound having the structure: <br> prepared according to Example IV | A fruity, green, gooseberry-like, apple, mushroom and kiwi aroma and taste profile at 2 ppm causing it to be useful in kiwi and gooseberry flavored foodstuffs. |
| Compound having the structure: <br> prepared according to Example V | An oniony, earthy, mushroom and radish aroma and oniony, earthy, mushroom, radish and salty taste profile causing it to be useful in onion, mushroom, sour cream and dairy foodstuffs as well as useful as a salt substitute. |

TABLE I-continued

THE 4 (HYDROCARBYLTHIO)
ACETOACETIC ESTERS
OF OUR INVENTION | FLAVOR PROPERTIES
--- | ---
Compound having the structure: 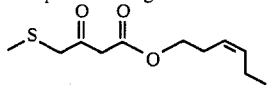 prepared according to Example VII | A fresh green, fruity, juicy, ripe tomato-like and potato skin-like aroma profile with a fresh green, fruity, juicy, ripe tomato-like, potato skin-like, ripe plum-like and radish-like taste profile at 1 ppm causing it to be useful in strawberry, plum, tomato, potato and tropical fruit flavored foodstuffs and chewing gums.
Compound having the structure: 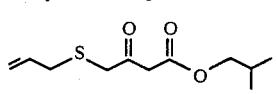 prepared according to Example VI | A garlic aroma and taste at 0.5 ppm.
Compound having the structure: 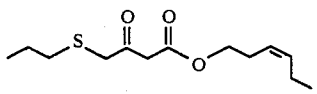 prepared according to Example VIII | A garlic, green pepper and fruity aroma and taste profile at 1 ppm causing it to be useful in green pepper and garlic flavors.

When the 4(hydrocarbylthio)acetoacetic esters produced according to the process of our invention are used as food flavor adjuvants, the nature of the co-ingredients included with the 4(hydrocarbylthio)acetoacetic esters used in formulating the product compositions will also serve to alter, modify, augment or enhance the organoleptic characteristics of the ultimate foodstuff treated therewith.

As used herein, in regard to flavors, the terms "alter", "modify" and "augment", in their various forms, means "supplying or imparting flavor character or note to otherwise blend relatively tasteless substances or augmenting the existing flavor characterist where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the 4(hydrocarbylthio)acetoacetic esters produced according to the process of our invention and, in addition, sweetening agents which may be sugars, including sucrose or dextrose and/or artificial sweeteners such as cyclamates or saccharins. Other optional ingredients may be present.

Substances for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may, in general, be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids, carbohydrates; starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate citric acid, lactic acid, vinegar and the like, colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benzaldehyde, $\beta$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons, such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2-3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as $\partial$-nonalactone; sulfides, e.g., methyl sulfide, propyl propenyl sulfide, allyl propenyl disulfide, allyl propenyl trisulfide, propyl propenyl trisulfide, propyl propenyl disulfide other thioesters and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the 4(hydrocarbylthio)acetoacetic esters of our invention by not covering or spoiling the organoleptic properties (aroma and/or taste) thereof; (ii) be non-reactive with one or more of the 4(hydrocarbylthio)acetoacetic esters of our invention and (iii) be capable of providing an environment in which the 4(hydrocarbylthio)acetoacetic esters of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste or chewing tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 4(hydrocarbylthio)acetoacetic esters or derivatives thereof of my invention employed in a particular instance can vary over a relatively wide range, depending upon the desired organoleptic effects to be achieved. Thus, correspondingly greater amounts would be necessary in those instances wherein the ultimate food composition to be flavored (e.g., a "raisin-rum cake") is relatively bland to the taste, whereas relatively minor quantities may suffice for purposes of enhancing the composition merely deficient in natural flavor or aroma, (e.g., when actual raisins and rum are present in the foodstuff such as the cake). The primary requirement is that the amount selected be effective, i.e. sufficient to alter, modify or enhance the organoleptic characteristic of the parent composition, whether foodstuff per se, chewing gum per se, medicinal product per se, toothpaste per se, chewing tobacco per se or flavoring composition.

The use of insufficient quantities of one or more 4(hydrocarbylthio)acetoacetic esters of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the content of the present invention consistent with the obtention of desired flavoring effects.

Thus, and with respect to ultimate food compositions, chewing gum compositions, medicinal product compositions, chewing tobacco compositions and toothpaste compositions, it is found that quantities of one or more 4(hydrocarbylthio)acetoacetic esters of our invention ranging from a small but effective amount, e.g., about 0.2 parts per million up to about 150 parts per million based on total food composition or chewing gum composition, and medicinal product composition or toothpaste composition or chewing tobacco composition are suitable. Concentrations in excess of the maximum quantity stated are not normally recommended since they fail to provide commensurate enhancement of organoleptic properties. In those instances where one or more 4(hydrocarbylthio)acetoacetic esters of our invention is added to the foodstuff as an integral component of a flavoring composition, it is, of course, essential that the total quantity of flavoring composition employed be sufficient to yield an effective concentration of one or more 4(hydrocarbylthio)acetoacetic esters of our invention in the foodstuff product.

Food flavoring compositions containing one or more of the compounds prepared in accordance with the present invention preferably contain one or more 4(hydrocarbylthio)acetoacetic esters in concentrations ranging from about 0.02% up to about 15% by weight of the total weight of said flavoring composition.

The compositions described herein can be presented according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more of the 4(hydrocarbylthio)acetoacetic esters prepared in accordance with our invention with, for example, gum arabic, gum tragacanth, xanthan gum, carrageenan and the like, and thereafter spray-drying the resultant mixture whereby to obtain the particulate solid product. Pre-prepared flavor mixes in powder form, e.g., a fruit flavored or rum flavored powder mix are obtained by mixing the dried solid components, e.g., starch, sugar and the like and one or more 4(hydrocarbylthio)acetoacetic esters of our invention in a dry blender until the requisite degree of uniformity is achieved.

It is presently preferred to combine one or more 4(hydrocarbylthio)acetoacetic esters of our invention with at least one of the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl Acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone(1-crotonyl-2,6,6-trimethylcyclohex-1-ene);
β-Damascenone(1-crotonyl-2,6,6-trimethylcyclohexa-1,3-diene);
Beta-cyclohomocitral(2,6,6-trimethylcyclohex-1-ene carboxaldehyde);

Isoamyl butyrate;
Cis-3-hexenol-1;
2-Methyl-2-pentenoic acid;
Elemecine(4-allyl-1,2,6-trimethoxybenzene);
Isoelemecine(4-propenyl-1,2,6-trimethoxybenzene);
2-(4-Hydroxy-4-methylpentyl)norbornadiene;
rum essence;
3-hydroxy butyric acid;
2-hydroxy butyric acid;
N-methyl anthranilate;
Cyclotene;
Ethyl cyclotene;
n-propyl cyclotene;
gin berry essence;
Dimethyl-disulfide;
Methyl-propyl disulfide;
Methyl-propenyl disulfide;
Dipropyl-disulfide;
Propyl-propenyl disulfide;
Diallyl-disulfide;
Acetyl methyl trisulfide;
Ethyl-4-(methylthio)butyrate;
4-(methylthio)butanol;
4-(methylthio)butanal;
Methyl-4-(methylthio)butyrate; and
1,1-diethoxy-4-(methylthio)butane.

The following Examples I–VIII set forth means for synthesizing the 4(hydrocarbylthio)acetoacetic of our invention. The Examples following Example VIII are illustrative of the organoleptic utilities of the 4(hydrocarbylthio)acetoacetic esters of our invention produced according to the processes of Examples I–VIII.

All parts and percentages given herein, are by weight unless otherwise specified.

EXAMPLE I

Preparation of ethyl-4-(methylthio)acetoacetate

Reaction:

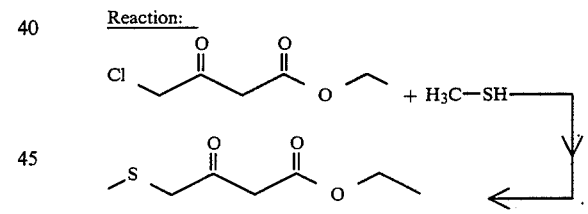

Into a 250 ml. reaction flask equipped with stirrer, thermometer and reflux condenser is placed 44 grams (0.2 moles) of sodium methylate, and 180 grams of methyl mercaptan including the 14.4 grams (0.3 moles) used as a reactant. The methyl mercaptan and sodium methoxide is admixed at room temperature for 30 minutes with cooling.

Into a separate 500 ml. reaction vessel equipped with stirrer, thermometer, addition funnel, reflux condenser and heating mantle is placed 32.8 grams (0.2 moles) of ethyl-4-chloroacetoacetate having the structure:

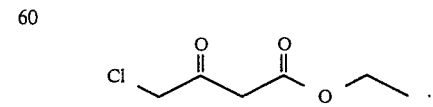

The premixture of methyl mercaptan and sodium methoxide is then poured into the addition funnel. Over a period of 30 minutes, the premixture of methyl mercaptan and sodium methoxide is fed into the 500 cc flask containing the ethyl-4-chloro acetoacetate while maintaining the pot temperature of 20°–30° C. As a result of the exothermic reaction, the reaction mass is cooled. After the addition of the methyl mercaptan-sodium methoxide mixture, the reaction mass is stirred for a period of 1 hour and the temperature of the reaction mass is permitted to rise to 41° C.

After the 1 hour period, 150 ml. water is added to the reaction mass and the reaction mass is then transferred to a separatory funnel, extracted with three 50 ml. volumes of methylene dichloride and then dried over anhydrous sodium sulfate. The resulting mixture is filtered and distilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 94 | 107 | 5 |
| 2 | 102 | 112 | 5 |
| 3 | 110 | 115 | 5 |
| 4 | 115 | 120 | 5 |
| 5 | 117 | 123 | 5 |
| 6 | 117 | 123 | 5 |
| 7 | 110 | 140 | 5 |

The resulting product has a gooseberry-like, mushroom-like, broccoli-like and pineapple-like aroma and taste profile at 1 ppm.

FIG. 1 is the GLC profile for fraction 6 of the foregoing distillation (Conditions: 10′×0.125″ SE-30 column programmed at 100°–220° C. at 8° C. per minute).

FIG. 2 is the NMR spectrum for the compound having the structure:

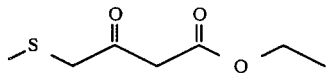

(Conditions: Field strength: 100 MHz; solvent: CFCl$_3$).

EXAMPLE II

Preparation of ethyl-4-(propylthio)acetoacetate

Reaction:

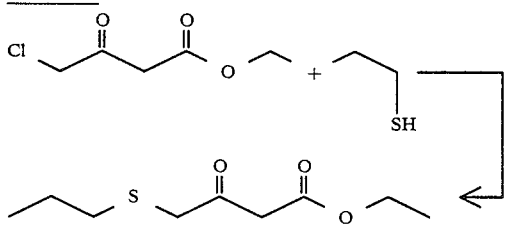

Into a 250 ml. reaction flask equipped with reflux condenser, spin bar and magnetic stirrer/hot plate is placed a mixture of 44 grams (0.2 moles) of sodium methoxide and 180 grams of n-propyl mercaptan including the 0.2 moles of n-propyl mercaptan used as reactant (15.2 grams). The resulting n-propyl mercaptan and sodium methoxide mixture is stirred for a period of 30 minutes.

Into a separate 500 ml. reaction flask equipped with electric stirrer, reflux condenser, thermometer, addition funnel and cooling bath is placed ethyl-4-chloro acetoacetate defined according to the structure:

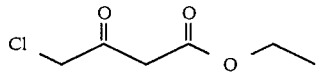

The ethyl-4-chloro acetoacetate is cooled to 20° C.

The premixed solution of n-propyl mercaptan and sodium methoxide is then placed in an addition funnel and is fed from the addition funnel into the 500 cc flask with stirring over a period of 30 minutes while maintaining the pot temperature at 20°–30° C. The reaction mass exotherm causing a need for cooling.

After the addition of the n-propyl mercaptan/sodium methoxide premix, the reaction mass is stirred for a period of 1 hour and the temperature of the reaction mass is permitted to rise to 45° C. After 1 hour, a GLC profile indicates that the reaction has gone to completion. 150 ml. of water is added to the reaction mass. The reaction mass is then transferred to a separatory funnel and the inorganic phase is extracted with 350 ml. portions of methylene dichloride. The methylene dichloride extract is combined with the organic phase and the resulting mixture is dried over anhydrous sodium sulfate, filtered and distilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 35 | 113 | 3 |
| 2 | 105 | 118 | 3 |
| 3 | 113 | 126 | 3 |
| 4 | 123 | 133 | 3 |
| 5 | 125 | 133 | 3 |
| 6 | 120 | 133 | 3 |
| 7 | 113 | 140 | 3 |

The resulting product has a fresh oniony aroma and taste profile at 1 ppm.

FIG. 3 is the GLC profile for fraction 5 of the foregoing distillation which contains the compound having the structure:

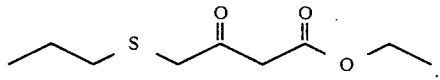

FIG. 4 is the NMR spectrum for fraction 5 of the foregoing distillation containing the compound having the structure:

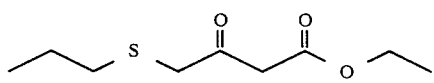

(Conditions: Field strength: 100 MHz; solvent: CFCl$_3$),

EXAMPLE III

Preparation of ethyl-4-(allylthio)acetoacetate

Reaction:

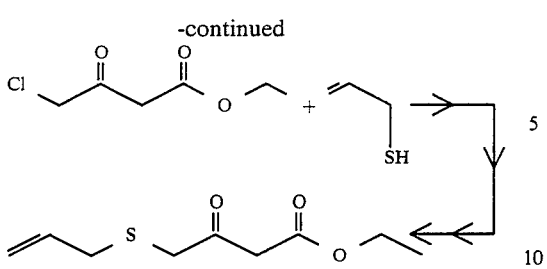

Into a 250 ml. reaction flask equipped with stirring bar, thermometer, reflux condenser and hot plate/stirring apparatus is placed a mixture of 44 grams (0.2 moles) of sodium methoxide and admixed with 180 grams of allyl mercaptan (including 14.8 grams [0.2 moles] for use as a reactant) and is placed in a 250 ml. reaction flask equipped with stirring bar, magnetic stirring apparatus, hot plate, thermometer and reflux condenser. The resulting mixture is stirred for a period of 0.5 hours.

Into a 500 ml. flask equipped with stirrer, thermometer, reflux condenser, cooling coils and heating mantle is placed 32.8 grams (0.2 moles) of ethyl-4-chloro acetoacetate having the structure:

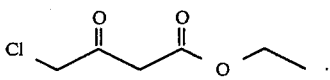

The ethyl-4-chloro acetoacetate is cooled to 20° C. The premix in the 250 ml. reaction flask of allyl mercaptan and sodium methoxide is poured into the addition funnel and over a 0.5 hour period, the allyl mercaptan/sodium methoxide premix is added to the ethyl-4-chloro acetoacetate in the 500 ml. flask while maintaining the pot temperature at 20°–30° C. The reaction exotherms and therefore needs cooling.

After the 0.5 hour addition period, the resulting reaction mass is stirred for a period of 1 hour while the temperature of reaction is permitted to rise to 48° C.

After the 1 hour period, the reaction mass is admixed with 150 ml. water and the resulting mixture is transferred to a separatory funnel. The aqueous phase is separated from the organic phase and the aqueous phase is extracted with three 50 ml. portions of methylene dichloride. The organic phases and methylene dichloride extracts are combined and dried over anhydrous sodium sulfate, filtered and distilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 72 | 116 | 15 |
| 2 | 118 | 132 | 15 |
| 3 | 126 | 137 | 15 |
| 4 | 126 | 147 | 15 |

The resulting product has an excellent cashew juice aroma and taste profile at 0.001 ppm causing it to be useful in cashew juice, pineapple, tropical fruit and apricot flavors.

FIG. 5 is the GLC profile for fraction 3 of the foregoing distillation (Conditions: 10′×0.125″ SE-30 column programmed at 100°–220° C. at 8° C. per minute).

FIG. 6 is the NMR spectrum for fraction 3 of the foregoing distillation containing the compound having the structure:

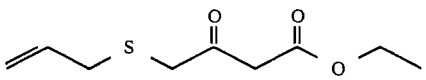

(Conditions: Field strength: 100 MHz; solvent: CFCl₃).

EXAMPLE IV

Preparation of isobutyl-4-(methylthio)acetoacetate

Reaction:

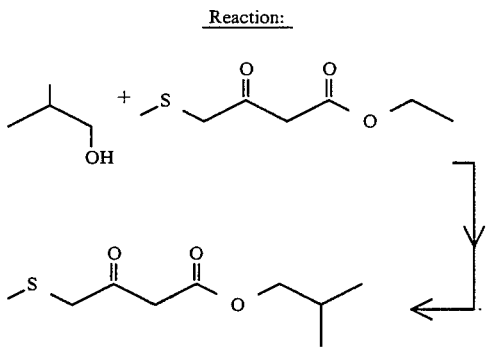

Into a 5 cc reaction flask equipped with spin bar, magnetic stirring hot plate, heating mantle, reflux condenser and thermometer is placed a mixture of:

| | |
|---|---|
| 5 grams ethyl-4-(methylthio)acetoacetate prepared according to Example I | 0.0284 moles |
| 8.4 grams isobutyl alcohol | 0.114 moles |
| 0.05 grams para-toluene sulfonic acid | |

The resulting mixture is heated to reflux and during reflux conversion is monitored using GLC (refluxing is continued for a period of 14 hours). At the end of the 14 hour period the reaction mass is cooled to room temperature. At this point in time the reaction is complete.

The reaction mass is transferred to a distillation flask and distilled on a one plate stone packed distillation column.

The resulting distillate is redistilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 25 | 40 | 6 |
| 2 | 97 | 107 | 6 |
| 3 | 105 | 116 | 6 |
| 4 | 95 | 130 | 6 |

The resulting product has a fruity, green, gooseberry-like, apple, mushroom and kiwi fruit aroma and taste profile at 2 ppm causing it to be useful in kiwi and gooseberry flavors.

FIG. 7 is the GLC profile for fraction 2 of the foregoing distillation containing the compound having the structure:

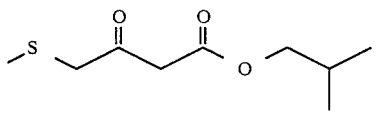

(Conditions: 10'×0.125" SE-30 column programmed at 100°–220° C. at 8° C. per minute).

FIG. 8 is the GLC profile for fraction 3 of the foregoing distillation containing the compound having the structure:

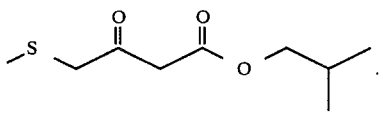

FIG. 9 is the GLC profile for fraction 4 of the foregoing distillation containing the compound having the structure:

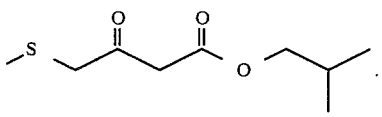

FIG. 10 is the NMR spectrum for fraction 4 of the foregoing distillation containing the compound having the structure:

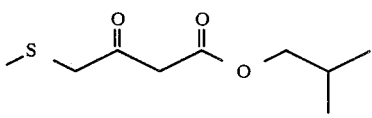

(Conditions: Field strength: 100 MHz; solvent: CFCl₃).

EXAMPLE V

Preparation of isobutyl-4-(propylthio)acetoacetate

Reaction:

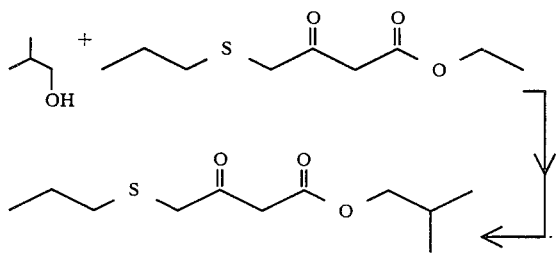

Into a 50 ml. reaction flask equipped with reflux condenser, spin bar, hot plate for magnetic stirring and heating mantle is placed:

| | |
|---|---|
| 5 grams ethyl-4-(propylthio)acetoacetate prepared according to Example II | 0.0245 moles |
| 7.2 grams isobutyl alcohol | 0.098 moles |
| 0.05 grams para-toluene sulphonic acid. | |

The reaction mass is heated to reflux and refluxed for a period of 20 hours. At the end of the refluxing, the reaction mass is transferred to a separatory funnel and washed with 150 ml. portion of water. The reaction mass is then dried over anhydrous sodium sulfate, filtered and distilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 117 | 136 | 6 |
| 2 | 111 | 170 | 6 |
| 3 | 114 | 185 | 6 |

The resulting reaction product has an oniony, earthy, mushroom and radish aroma with an oniony, earthy, mushroom, radish and salty taste profile causing it to be useful in onion, mushroom, sour cream and dairy flavors and as a salt substitute.

FIG. 11 is the GLC profile for the crude reaction product containing the compound having the structure:

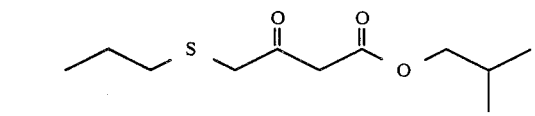

(Conditions: 10'×0.125" SE-30 column programmed at 100°–220° C. at 8° C. per minute).

FIG. 12 is the GLC profile for fraction 2 of the foregoing distillation containing the compound having the structure:

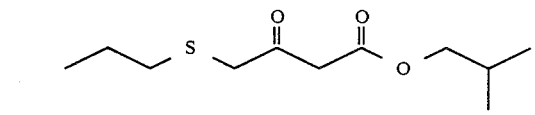

(Conditions: 10'×0.125" SE-30 programmed at 100°–220° C. at 8° C. per minute).

FIG. 13 is the NMR spectrum for fraction 2 of the foregoing distillation containing the compound having the structure:

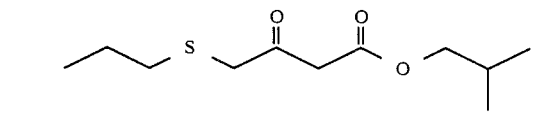

(Conditions: Field strength: 100 MHz; solvent: CFCl₃).

EXAMPLE VI

Preparation of isobutyl-4-(allylthio)acetoacetate

Reaction:

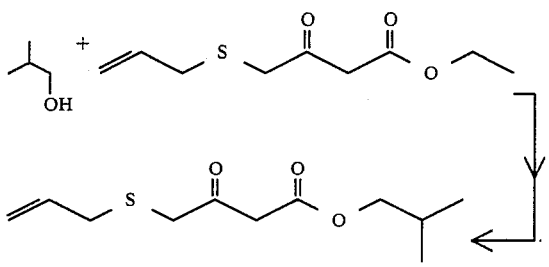

Into a 50 cc reaction flask equipped with spin bar, magnetic stirrer, hot plate, heating mantle, reflux condenser and thermometer is placed the following materials:

| | |
|---|---|
| 5 grams ethyl-4-(allylthio)aceto-acetate prepared according to Example III | 0.0245 moles |
| 7.3 grams isobutanol | 0.099 moles |
| 0.05 grams para-toluene sulfonic acid | |

The reaction mixture is heated to reflux and refluxed for a period of 15 hours while being monitored for conversion by using a GLC apparatus (Conditions: 10'×0.125" SE-30 column programmed at 100°-220° C. at 8° C. per minute).

At the end of the 15 hour period it was indicated that the reaction is complete.

The reaction mass is transferred to a distillation flask and distilled on a one plate short path column and then redistilled on a micro vigreux column yielding the following four fractions:

| FRACTION NUMBER | VAPOR TEMP. (°C.) | LIQUID TEMP. (°C.) | VACUUM PRESSURE mm/Hg. |
|---|---|---|---|
| 1 | 23 | 25 | 6 |
| 2 | 102 | 125 | 6 |
| 3 | 116 | 133 | 6 |
| 4 | 110 | 140 | 6 |

FIG. 14 is the GLC profile for the crude reaction product containing the compound having the structure:

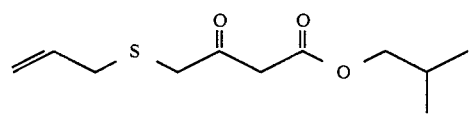

(Conditions: 10'×0.125" SE-30 column programmed at 100°-220° C. at 8° C. per minute).

FIG. 15 is the GLC profile for fraction 4 of the foregoing distillation containing the compound having the structure:

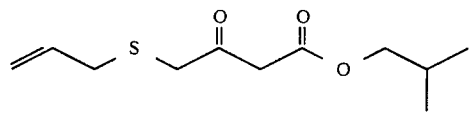

(Conditions: 10'×0.125" SE-30 column programmed at 100°-220° C. at 8° C. per minute).

FIG. 16 is the NMR spectrum for fraction 4 of the foregoing distillation containing the compound having the structure:

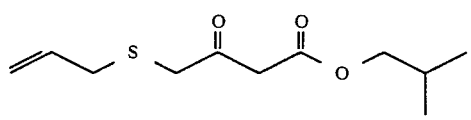

(Conditions: Field strength: 100 MHz; solvent: CFCl₃).

EXAMPLE VII

Preparation of cis-3-hexenyl-4-(methylthio)acetoacetate

Reaction:

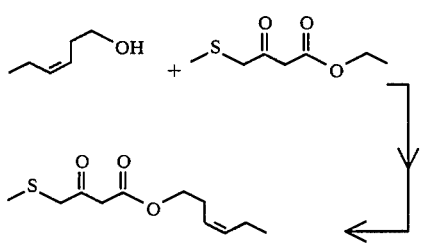

Into a 50 ml. reaction flask equipped with spin bar, magnetic stirrer/hot plate, reflux condenser, heating mantle and thermometer is placed the following materials:

| | |
|---|---|
| 5 grams ethyl-4-(methylthio)aceto-acetate prepared according to Example I | 0.0284 moles |
| 11.4 grams cis-3-hexenol | 0.114 moles |
| 0.05 grams para-toluene sulfonic acid | |

The reaction mass is heated to reflux and refluxed for a period of 15 hours while the conversion is being monitored by means of GLC (10'×0.125" SE-30 column programmed at 100°-220° C. at 8° C. per minute).

At the end of the 15 hour period the reaction mass is cooled and transferred to a distillation flask. The reaction mass is distilled on a one plate short path column and the resultant distillate is redistilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 38 | 45 | 6 |
| 2 | 83 | 122 | 6 |
| 3 | 118 | 145 | 6 |
| 4 | 132 | 152 | 6 |
| 5 | 133 | 157 | 6 |
| 6 | 124 | 170 | 6 |

The resulting product has a fresh green, fruity, juicy, ripe tomato-like and potato skin-like aroma profile with a fresh green, fruity, juicy, ripe tomato-like, potato skin-like, ripe plum-like and radish-like taste profile at 1 ppm causing it to be useful in strawberry, plum, tomato, potato and tropical fruit flavors.

FIG. 17 is the GLC profile for the crude reaction product containing the compound having the structure:

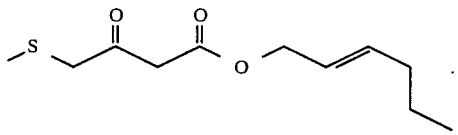

FIG. 18 is the GLC profile for fraction 5 of the foregoing distillation containing the compound having the structure:

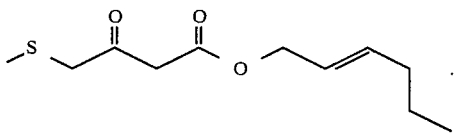

FIG. 19 is the NMR spectrum for fraction 5 of the foregoing distillation containing the compound having the structure:

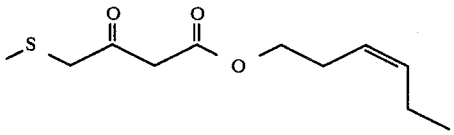

(Conditions: Field strength: 100 MHz; solvent: CFCl$_3$).

EXAMPLE VIII

Preparation of cis-3-hexenyl-4-(propylthio)acetoacetate

Reaction:

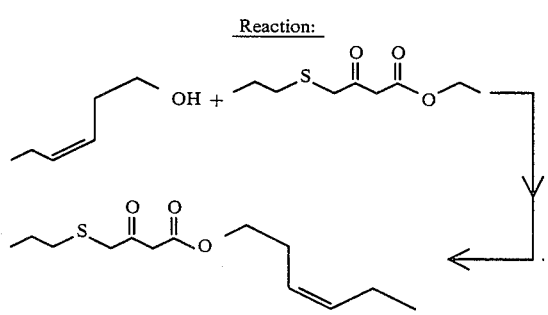

Into a 50 cc reaction flask equipped with spin bar, magnetic stirring/hot plate apparatus, heating mantle, reflux condenser and thermometer is placed:

| | |
|---|---|
| 5 grams ethyl-4-(propylthio)aceto-acetate prepared according to Example II | 0.0245 moles |
| 9.8 grams cis-3-hexenol | 0.098 moles |
| 0.05 grams para-toluene sulfonic acid | |

The reaction mass is heated to reflux and refluxed for a period of 13.5 hours while a conversion is being monitored by means of GLC (Conditions: 10′×0.125″ SE-30 column programmed at 100°-220° C. at 8° C. per minute).

At the end of this period of time the reaction mass is complete and the reaction mass is cooled to room temperature and transferred to a distillation flask and distilled on a one plate short path column. The resulting distillate is then redistilled on a micro vigreux column yielding the following fractions:

| FRACTION NUMBER | VAPOR TEMP. (°C.) | LIQUID TEMP. (°C.) | VACUUM PRESSURE mm/Hg. |
|---|---|---|---|
| 1 | 32 | 35 | 6 |
| 2 | 90 | 140 | 6 |
| 3 | 110 | 157 | 6 |
| 4 | 140 | 180 | 6 |
| 5 | 130 | 195 | 6 |

FIG. 20 is the GLC profile for the crude reaction product containing the compound having the structure:

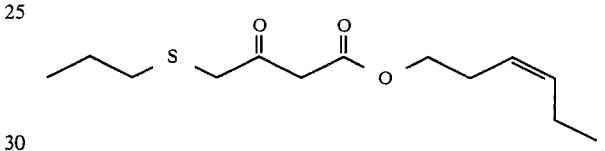

FIG. 21 is the GLC profile for fraction 3 of the foregoing distillation product containing the compound having the structure:

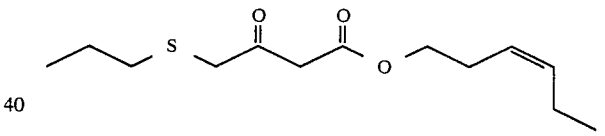

FIG. 22 is the GLC profile for fraction 4 of the foregoing distillation product containing the compound having the structure:

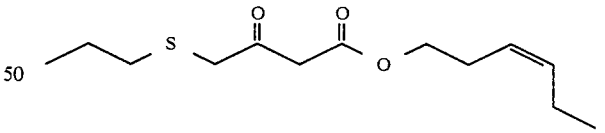

FIG. 23 is the NMR spectrum for fraction 4 of the foregoing distillation product containing the compound having the structure:

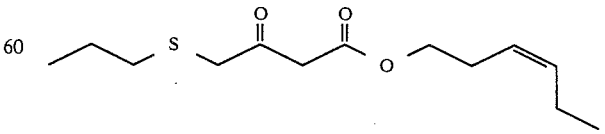

(Conditions: Field strength: 100 MHz; solvent: CFCl$_3$).

EXAMPLE IX

The compound having the structure:

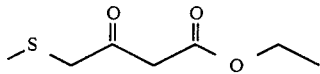

prepared according to Example I is added to a commercially available mushroom soup at the rate of 1.0 ppm and compared by a bench panel (consisting of four individuals) with an unflavored control. The soup flavored with the compound having the structure:

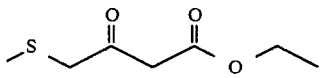

has a stronger mushroom aroma and taste (masking the starch and flour notes present) and is preferred as being more mushroom-like.

EXAMPLE X(A)

The following ingredients are admixed:

| INGREDIENTS | PARTS PER 100 TOTAL |
|---|---|
| Dimethyl disulfide | 4 |
| Methyl propyl disulfide | 25 |
| Methyl propenyl disulfide | 2 |
| Dipropyl disulfide | 30 |
| Propyl propenyl disulfide | 8 |
| Diallyl disulfide | 1 |
| Compound having the structure: 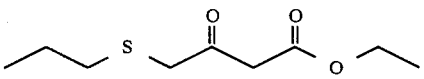 prepared according to Example II | 8 |

The ingredients are thoroughly and homogeneously mixed to 25° C. This mixture has an excellent fresh onion flavor definitely enhanced over that obtained when the compound having the structure:

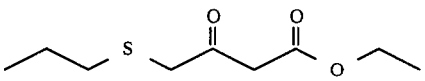

prepared according to Example II is omitted.

EXAMPLE X(B)

The composition of Example X(A) is dissolved in propylene glycol in an amount sufficient to give a propylene glycol solution containing 0.1% by weight of said mixture. 0.9 cc of this solution is added to 7.3 grams of a soup base consisting of:

| INGREDIENTS | PARTS PER 100 QUANTITY |
|---|---|
| Fine ground sodium chloride | 35.62 |
| Hydrolyzed vegetable protein (4BE: NESTLE'S) | 27.40 |
| Monsodium glutamate | 17.81 |
| Sucrose | 10.96 |
| Beef fat | 5.48 |
| Sethness caramel color (powder B & C) | 2.73 |

The resulting mixture is added to 12 oz. of boiling water to create a soup having an excellent fresh onion flavor.

A composition not containing the compound having the structure:

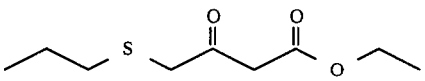

when added to the above soup base yields a soup having an onion flavor which is deficient in the very fresh onion notes that cause this onion soup to be highly desirable.

EXAMPLE XI

Into 15 oz. of GOYA ® Mango Nectar (Registered trademark of the GOYA Company of New York, N.Y.) at the rate of 0.003 ppm is placed the compound defined according to the structure:

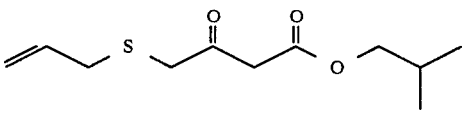

produced according to Example III.

The compound having the structure:

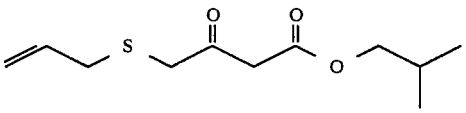

imparts to this mango nectar an excellent cashew note which causes the mango nectar to be much more natural-like and aesthetically pleasing. A similar result is created when the compound having the structure:

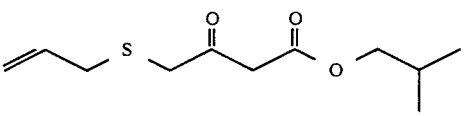

is added to KRASDALE ® Apricot Nectar at the rate of 0.005 ppm. The resulting apricot nectar has an excellent tropical fruit nuance and is much more natural-like.

EXAMPLE XII

The compound having the structure:

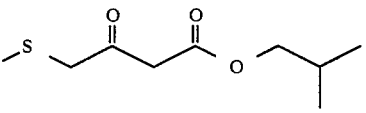

prepared according to Example IV is added at the rate of 3 ppm to gooseberry preserves. A natural tropical fruit apple-like kiwi fruit-like nuance is imparted to the gooseberry preserves causing it to be more aesthetically pleasing and natural-like even when permitted to remain refrigerated in an open container for a period of three weeks at 32° F.

EXAMPLE XIII

The following ingredients are selected:

| INGREDIENTS | PARTS PER 100 QUANTITY |
|---|---|
| Methyl propyl disulfide | 2.0 |
| Methyl propenyl disulfide | 0.5 |
| Dipropyl disulfide | 45.0 |
| Propyl propenyl disulfide | 4.0 |
| Diallyl disulfide | 0.5 |
| The compound having the structure: 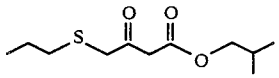 prepared according to Example V | 35.0 |

The ingredients are thoroughly and homogeneously mixed to 25° C.

0.5 Grams of the resulting mixture is emulsified in a solution containing the following materials:
100 grams gum arabic
300 grams water
0.5 grams 20 percent solution in ethanol of butylated hydroxy anisol.

The resultant emulsion is spray dried in a Bowen Lab. Model spray-drier, inlet temperature 500° F., outlet temperature 200° F. 12 Grams of this spray-dried material is mixed with 29.2 grams of the following soup base:

| INGREDIENTS | PARTS PER 100 QUANTITY |
|---|---|
| Fine ground sodium chloride | 35.62 |
| Hydrolyzed vegetable protein (4 BE: NESTLE'S) | 27.40 |
| Mono potassium glutamate | 17.81 |
| Mono calcium glutamate | 17.81 |
| Sucrose | 10.96 |
| Beef fat | 5.48 |
| Sethness caramel color [powder B & C] | 2.73 |

The resulting mixture is then added to boiling water and an excellent onion flavor with earthy and radish nuances is created. When the sodium chloride is omitted from the soup base mixture and the quantity of the compound having the structure:

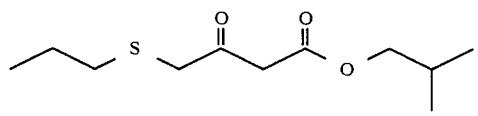

is doubled, the compound having the structure:

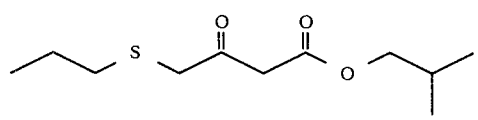

acts as a sodium chloride replacer when the calcium glutamate and the potassium glutamate are present. The resulting soup also has earthy and mushroom nuances.

EXAMPLE XIV

The compound having the structure:

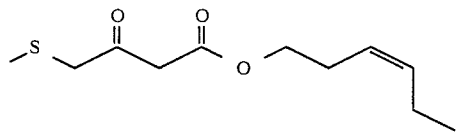

produced according to Example VII is added to commercially available tomato soup at the rate of 1 pm. The compound having the structure:

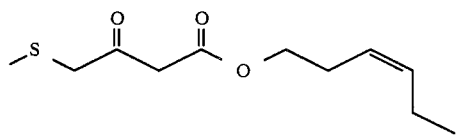

is found to add the aroma and taste of fresh ripe tomatos to the soup overcoming the flour and starch notes of the soup.

EXAMPLE XV

Pineapple Flavor

The following pineapple flavor is prepared:

| INGREDIENTS | PARTS BY WEIGHT |
|---|---|
| 2,5-dimethyl-4-hydroxy-3-[2H]—furanone | 45.0 |
| p-allyl phenol | 5.0 |
| Gamma-caprolactone | 3.0 |
| Gamma-decalactone | 3.8 |
| Delta-decalactone | 4.0 |
| Delta-undecalactone | 8.4 |
| Methyl beta-methylthio propionate | 4.2 |
| Ethyl beta-methylthio propionate | 4.4 |
| Methyl beta-hydroxy caprolate | 4.2 |
| Methyl beta-acetoxy caprolate | 3.2 |
| The compound having the structure: | 7.3 |

The resulting mixture has an excellent pineapple flavor. The resulting flavor is unexpectedly stable over long periods of time and is therefore useful in flavoring chewing gums, toothpastes and medicinal products.

EXAMPLE XVI

A. Powder Flavor Formulation

20 Grams of the flavor composition of Example XV is emulsified in a solution containing 300 grams of gum acacia and 70 grams water. The emulsion is spray-dried with a Bowen Lab. Model Drier utilizing 260 c.f.m. of air with an inlet temperature of 200° F. and a wheel speed of 50,000 rpm.

B. Sustained Release Flavor

| INGREDIENTS | PARTS BY WEIGHT |
|---|---|
| Liquid pineapple flavor of Example XV | 20.0 |
| Propylene glycol | 9.0 |

| INGREDIENTS | PARTS BY WEIGHT |
|---|---|
| Cab-O-Sil ® M-5 <br> (Brand of Silica produced <br> by the Cabot Corporation of <br> 125 High Street, Boston, <br> Mass. 02110 <br> Physical properties: <br> Surface area: 200 m²/gm <br> Nominal particle size (0.012 microns <br> Density: 2.3 lbs/cu. ft.) | 5.0 |

The cab-O-Sil ® is dispersed in the liquid pineapple flavor composition of Example XV with vigorous stirring, thereby resulting in a viscous liquid. 71 Parts by weight of the powder flavor composition of Part A, supra, is then blended into the said viscous liquid, with stirring, at 25° C., for a period of 30 minutes resulting in a dry, free-flowing sustained release flavor powder.

EXAMPLE XVII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XV is added to the solution which is then homogenized to form an emulsion having particle size typically in the range of 5–40 microns. This material is kept at 120° F. under which conditions the gelatin will not jell.

Coacervation is induced by adding, slowly and uniformly 40 parts by weight of a 20% aqueous solution of sodium sulfate. During coacervation, the gelatin molecules are deposited uniformly about each oil droplet as a nucleus.

Gelatin is effected by pouring the heated coacervate mixture into 1,000 parts by weight of 7% aqueous solution of sodium sulfate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XVIII

Chewing Gum

100 Parts by weight of chicle are mixed with 4 parts by weight of the flavor prepared in accordance with Example XVI(B). 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting pineapple flavor.

EXAMPLE XIX

Chewing Gum

100 Parts by weight of chicle are mixed with 18 parts by weight of the flavor prepared in accordance with Example XVII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting pineapple flavor.

EXAMPLE XX

Toothpaste Formulation

The following separate groups of ingredients are prepared:

| INGREDIENTS | PARTS BY WEIGHT |
|---|---|
| Group "A" | |
| Glycerine | 30.200 |
| Distilled Water | 15.325 |
| Sodium Benzoate | .100 |
| Saccharin Sodium | .125 |
| Stannous Fluoride | .400 |
| Group "B" | |
| Calcium Carbonate | 12.500 |
| Dicalcium Phosphate <br> (Dihydrate) | 37.200 |
| Group "C" | |
| Sodium N—Lauroyl Sarcosinate <br> (foaming agent) | 2.000 |
| Group "D" | |
| Flavor Material of Example XVI (B) | 1.200 |
| (Total) | 100.000 |

Procedure

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste if formed
4. With stirring, the flavor of "D" is added and lastly the sodium n-lauroyl sarcosinate
5. The resultant slurry is then blended for one hour.

The completed paste is then transferred to a three roller mill and then homogenized, and finally tubed.

The resulting toothpaste when used in a normal toothbrushing procedure yields a pleasant pineapple flavor of constant strong intensity throughout said procedure (1–1.5 minutes).

EXAMPLE XXI

Green Pepper Flavor and Use

The following green pepper flavor formulation is prepared:

| INGREDIENTS | PARTS BY WEIGHT |
|---|---|
| Methoxy isobutyl pyrazine | 50.0 |
| The compound having <br> the structure: | 50.0 |

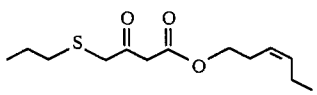

At the rate of 1 ppm the foregoing formulation is added to an "oil and vinegar" salad dressing. The plan oil and vinegar salad dressing now has an excellent green pepper and garlicky aroma and taste profile and is preferred by a bench panel of four members who are not associated with the inventorship entity or the assignee of the above-identified application.

When the compound having the structure:

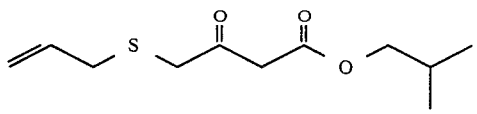

prepared according to Example VI is added to the salad dressing at the level of 0.5 ppm, the intensity of the garlic aroma and taste is increased threefold and a more natural-like garlic flavor is imparted to the salad dressing.

When the foregoing salad dressing containing the compounds having the structures:

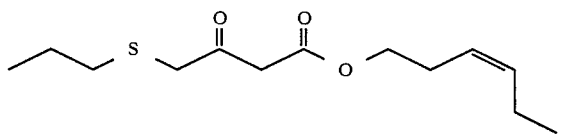

and

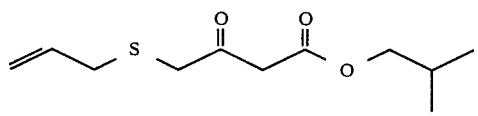

is added at the level of 10% by weight to a salad consisting of:

| INGREDIENT | PARTS BY WEIGHT |
|---|---|
| A. Lettuce | 50% |
| B. Sliced avocado | 40% |
| C. Blue cheese | 10% | the aroma and taste of the resulting salad is greatly improved and made more aesthetically pleasing. A bench panel of four members unanimously prefers the resulting salad over the salad without regressing or over the same salad with a plain oil and vinegar dressing.

What is claimed is:

1. The 4(hydrocarbylthio)acetoacetic ester having the structure:

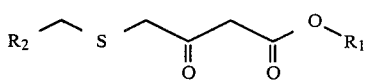

wherein $R_1$ represents cis-3-hexenyl and $R_2$ is selected from the group consisting of hydrogen and ethyl.

2. The 4(hydrocarbylthio)acetoacetic ester of claim 1 wherein $R_2$ is hydrogen.

3. The 4(hydrocarbylthio)acetoacetic ester of claim 1 wherein $R_2$ is ethyl.

4. The 4(hydrocarbylthio)acetoacetic ester having the structure:

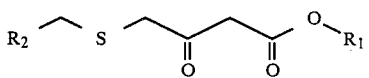

wherein $R_1$ is selected from the group consisting of ethyl and isobutyl and $R_2$ is vinyl.

5. The 4(hydrocarbylthio)acetoacetic ester of claim 4 wherein $R_1$ is isobutyl.

6. The 4(hydrocarbylthio)acetoacetic ester of claim 4 wherein $R_1$ is ethyl.

* * * * *